US008859257B2

(12) United States Patent
Hausmann et al.

(10) Patent No.: US 8,859,257 B2
(45) Date of Patent: Oct. 14, 2014

(54) VACCINIA VIRUS MUTANTS CONTAINING THE MAJOR GENOMIC DELETIONS OF MVA

(75) Inventors: Jürgen Hausmann, Gundelfingen (DE); Christine Meisinger-Henschel, Neuried (DE); Mark Suter, Lucerne (CH)

(73) Assignee: Bavarian Nordic A/S, Kvistgaard (DK)

( * ) Notice: Subject to any disclaimer, the term of this patent is extended or adjusted under 35 U.S.C. 154(b) by 46 days.

(21) Appl. No.: 13/575,773

(22) PCT Filed: Jan. 28, 2011

(86) PCT No.: PCT/EP2011/000405
§ 371 (c)(1),
(2), (4) Date: Jul. 27, 2012

(87) PCT Pub. No.: WO2011/092029
PCT Pub. Date: Aug. 4, 2011

(65) Prior Publication Data

US 2012/0308995 A1 Dec. 6, 2012

Related U.S. Application Data

(60) Provisional application No. 61/298,942, filed on Jan. 28, 2010.

(30) Foreign Application Priority Data

Jul. 8, 2010 (EP) .................................... 10007063

(51) Int. Cl.

| | |
|---|---|
| ***C12N 7/00*** | (2006.01) |
| ***C12N 15/863*** | (2006.01) |
| ***C12N 15/70*** | (2006.01) |
| ***C12N 15/64*** | (2006.01) |
| ***C12N 1/21*** | (2006.01) |
| ***C12N 5/10*** | (2006.01) |
| ***C12Q 1/70*** | (2006.01) |
| ***C12N 7/02*** | (2006.01) |
| ***C12N 15/86*** | (2006.01) |
| *A61K 39/00* | (2006.01) |

(52) U.S. Cl.
CPC ........ *C12N 7/00* (2013.01); *C12N 2710/24162* (2013.01); *C12N 2710/24121* (2013.01); *C12N 7/02* (2013.01); *C12N 2710/24151* (2013.01); *A61K 2039/525* (2013.01); *C12N 15/86* (2013.01); *C12N 2710/24143* (2013.01)
USPC ......... 435/235.1; 435/5; 435/471; 435/320.1; 435/325; 435/252.3

(58) Field of Classification Search
CPC ............. A61K 2039/525; C12N 15/86; C12N 2710/24121; C12N 2710/24143; C12N 2710/24151; C12N 2710/24162; C12N 7/00; C12N 7/02
See application file for complete search history.

(56) References Cited

FOREIGN PATENT DOCUMENTS

WO WO 2010/031837 * 3/2010

OTHER PUBLICATIONS

Meisinger-Henschel et al (Journal of General Virology 88:3249-3259, 2007) (in IDS).*
Cottingham et al (Plos One 3(2) e1638, pp. 1-10, 2008).*
European Search Report for EP Application No. 10007063.0, issued Nov. 19, 2010.
International Search Report for PCT Application No. PCT/EP2011/000405, issued Apr. 8, 2011.
C. Meisinger-Henschel et al., "Genomic sequence of chorioallantois vaccinia virus Ankara, the ancestor of modified vaccinia virus Ankara," *J. Gen. Virol.* 88:3249 3259 (2007).
M.E. Perkus et al., "Deletion of 55 open reading frames from the termini of vaccinia virus," *Virol.* 180(1):406-410 (1991).
M. Suter et al., "Modified vaccinia Ankara strains with identical coding sequences actually represent complex mixtures of viruses that determine the biological properties of each strain," *Vaccine* 27:7442-7450 (2009).
L.S. Wyatt et al., "Marker rescue of the host range restriction defects of modified vaccinia virus Ankara," *Virol.* 251(2):334-342 (1998).

* cited by examiner

*Primary Examiner* — Mary E Mosher
(74) *Attorney, Agent, or Firm* — Law Office of Salvatore Arrigo and Scott Lee, LLP

(57) ABSTRACT

The present invention provides modified vaccinia virus (VACV) genomes as well as vectors, especially viral vectors comprising the same. The present invention further provides modified vaccinia viruses. The present invention further provides methods for determining the effect of mutations in VACV with regard to competence for replication in certain cell types. The present invention further provides methods of preparing modified vaccinia viruses.

23 Claims, 17 Drawing Sheets

A

Figure 4I:
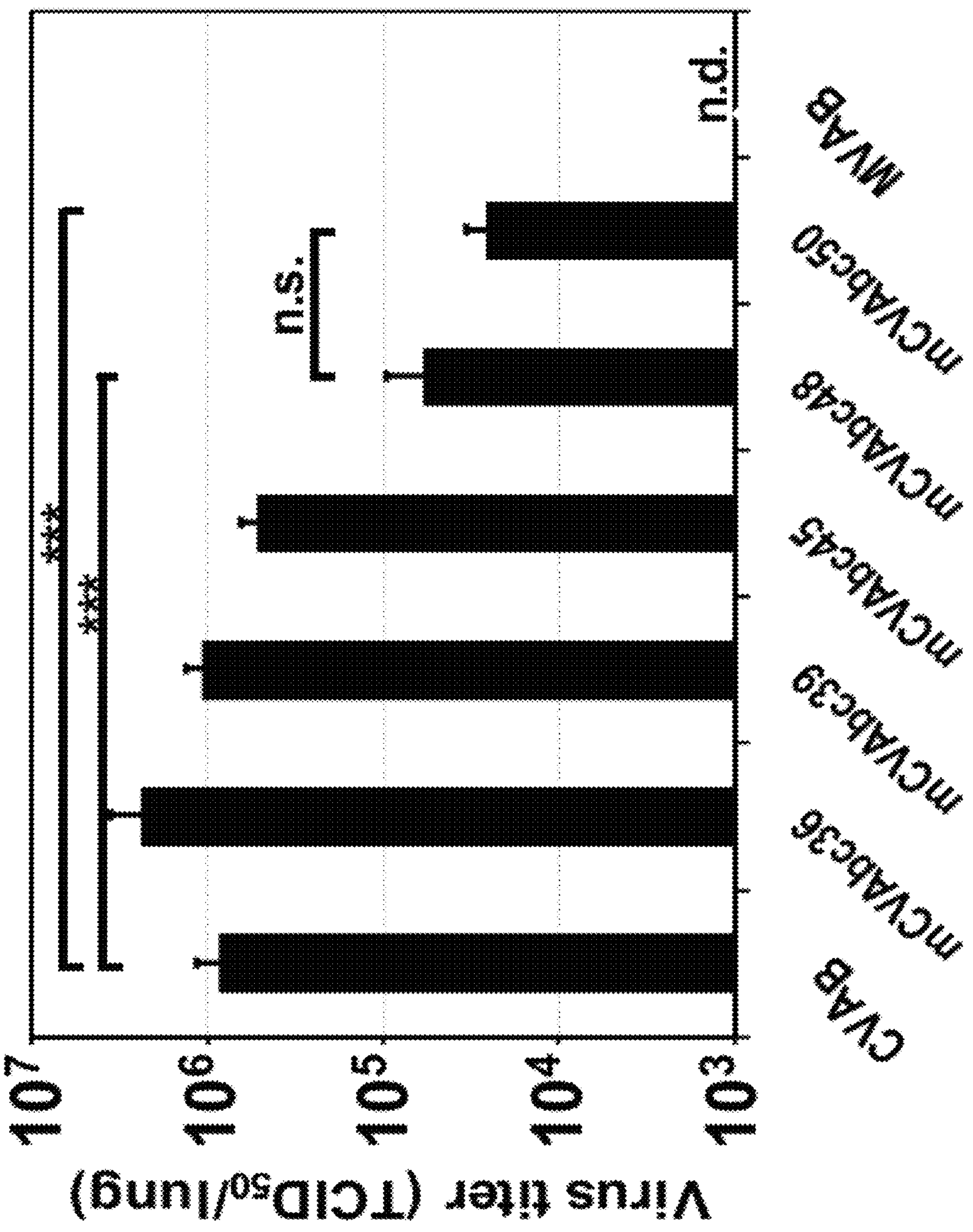

Fig. 4A-B
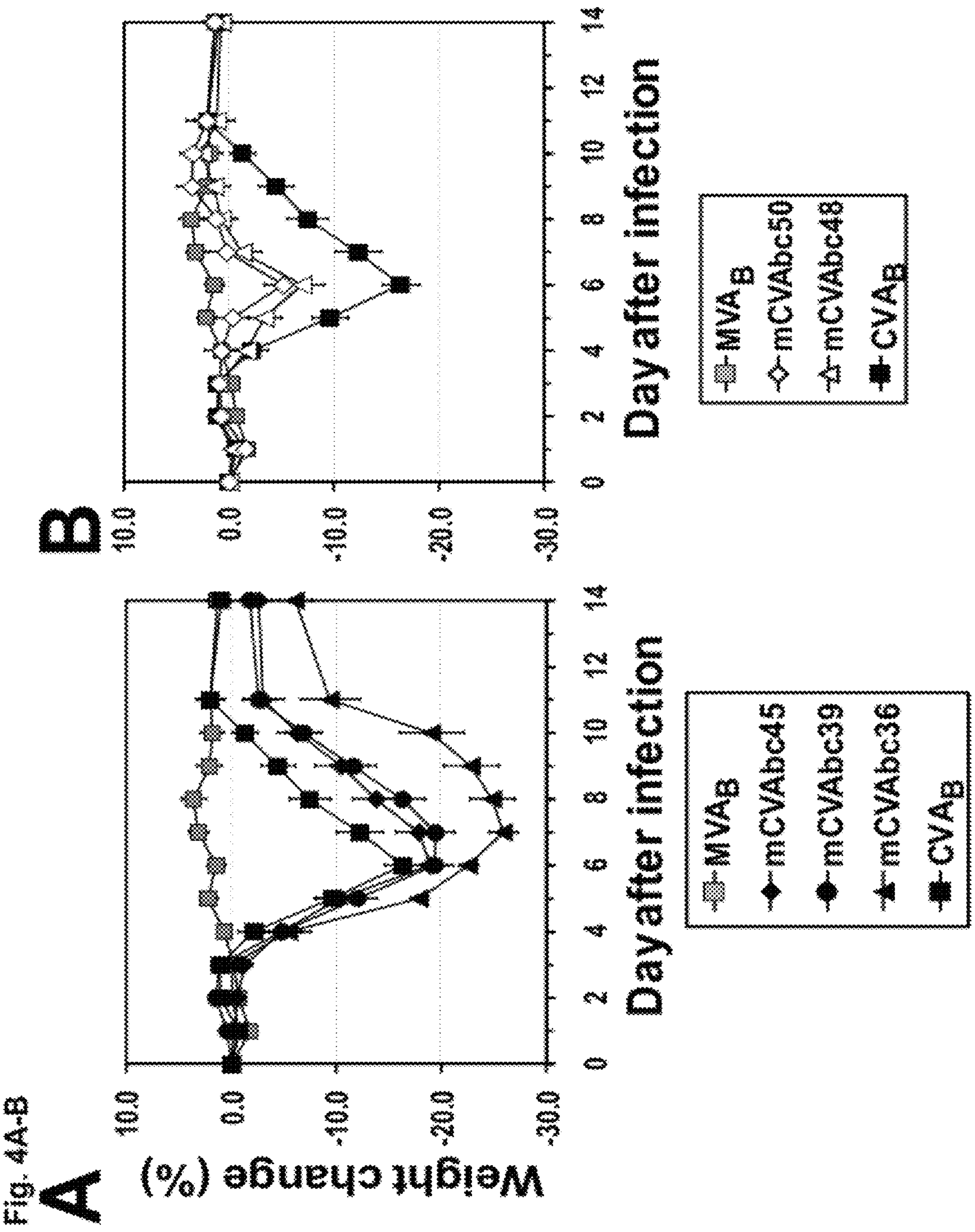

Fig. 4C-D
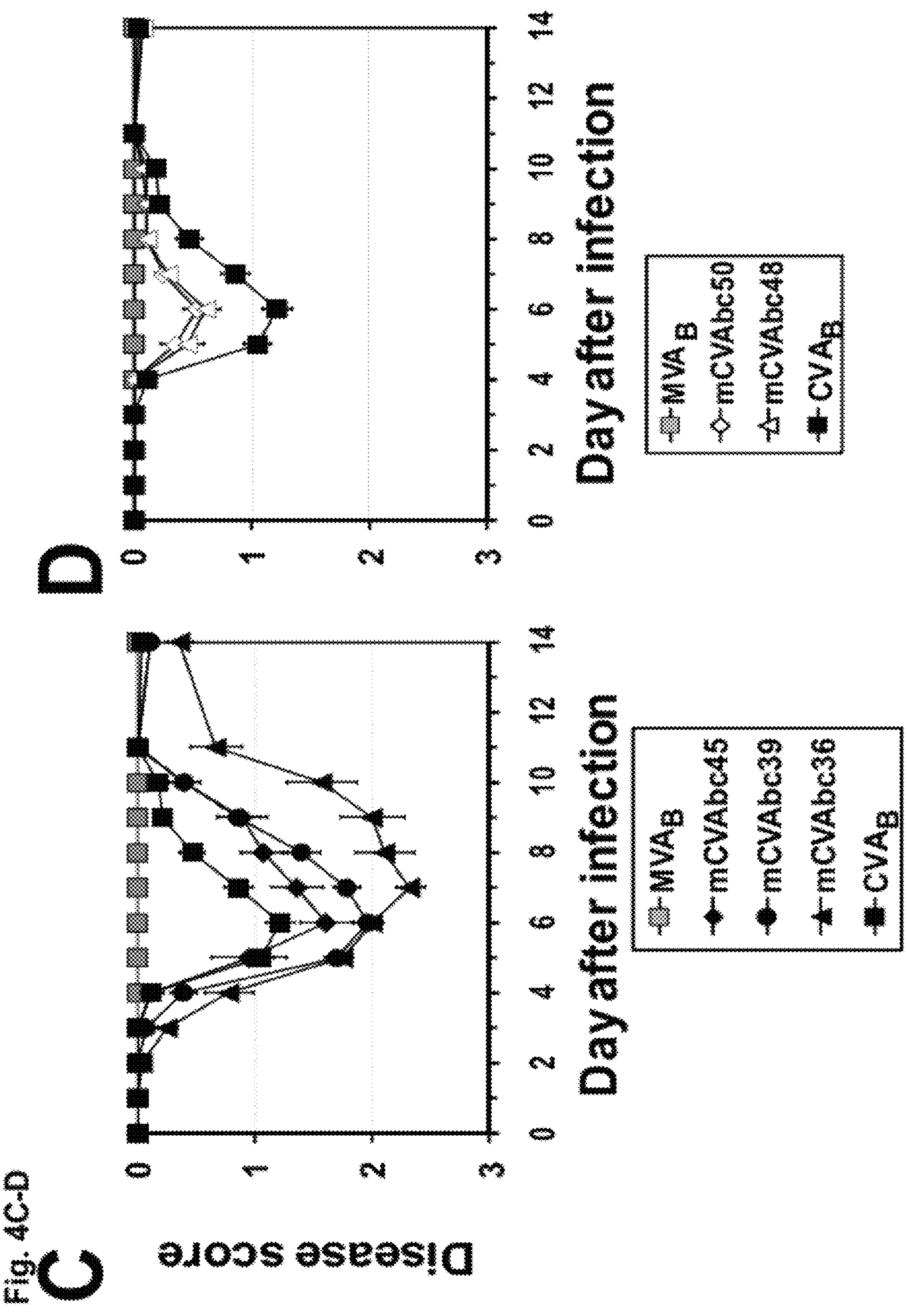

Fig. 4E-F
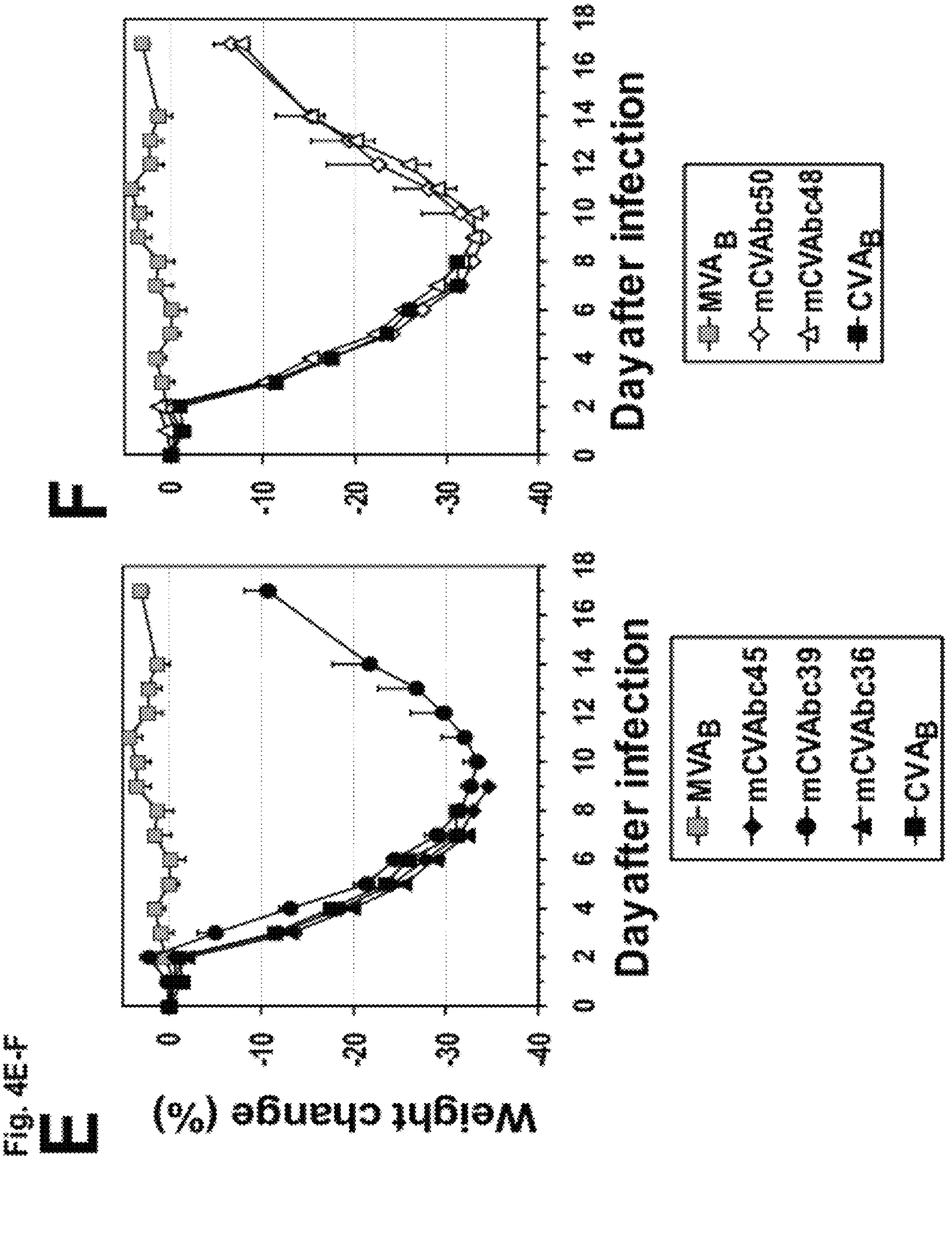

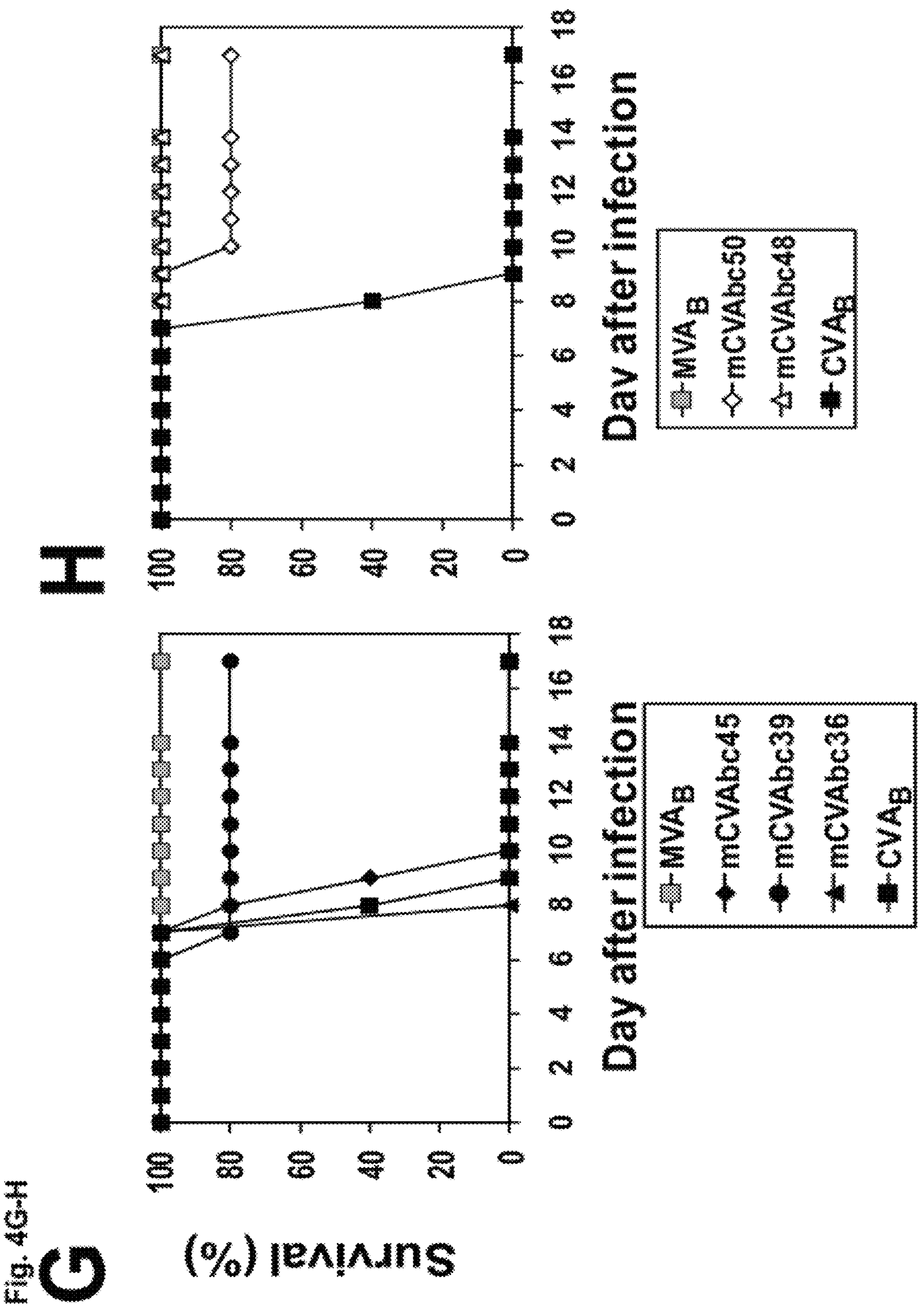
Fig. 4G-H
G
H
Survival (%)
100
80
60
40
20
0
0 2 4 6 8 10 12 14 16 18
Day after infection
MVA_B
mCVAbc45
mCVAbc39
mCVAbc36
CVA_B
mCVAbc50
mCVAbc48

VACCINIA VIRUS MUTANTS CONTAINING THE MAJOR GENOMIC DELETIONS OF MVA

This application is a National Phase application under 35 U.S.C. §371 of International Application No. PCT/EP2011/000405, filed Jan. 28, 2011, and claims the benefit under 35 U.S.C. §365 of European Application No. 10007063.0, filed Jul. 8, 2010, and the benefit under 35 U.S.C. §119(e) of U.S. Provisional Application No. 61/298,942, filed Jan. 28, 2010, the disclosures of which are incorporated herein by reference in their entirety.

The present invention provides modified vaccinia virus (VACV) genomes as well as vectors, especially viral vectors comprising the same. The present invention further provides modified vaccinia viruses. The present invention further provides isolated cells comprising any of the above materials, methods for determining the effect of mutations in VACV with regard to i.a. competence for replication in certain cell types. The present invention further provides methods of preparing modified vaccinia viruses.

During the 1970's the pioneering work of Mayr and associates led to the development of safer vaccines against poxvirus infections (29,30). This was achieved by continually passaging the chorioallantois vaccinia virus Ankara (CVA) on chicken embryo fibroblast (CEF) cells; after more than 570 such passages, the virus was re-named "Modified Vaccinia Ankara" (MVA) virus (16,17). The safety and immunogenicity of this virus has been tested extensively and both the limited ability to replicate as well as the neuropathogenicity of MVA in humans and other mammals has been described in various publications (1,16-18,20,29). Based on these reports, it has been generally concluded that after the 570th passage on CEF cells MVA is uniform and genetically stable (16), an assertion that is widely accepted today (21,29).

These conclusions were supported by DNA mapping of MVA and its ancestor CVA by enzyme digests, which revealed six deletions within the MVA genome resulting in an estimated loss of 30 kb of DNA compared to CVA (2,20). The nucleotide sequence of MVA has been determined, and the genes annotated and compared to the Vaccinia Copenhagen strain (3). The MVA genome, which has been computed to be 177 kb, allowed a more detailed analysis of deleted and altered genes. These data revealed the absence of some mammalian host range genes in MVA, which was taken as direct evidence for the limited replication in mammalian cells (3).

In addition to the six major large deletions mentioned above, many smaller mutations such as gene fragmentations, truncations and point mutations occurred in passaging CVA to MVA, and such mutations could account for the attenuated phenotype of MVA (19). MVA no longer encodes many of the known poxyiral immune evasion and virulence factors (3) but how this determines its abortive phenotype in mammalian cells and its lack of pathogenicity in vivo is not understood. Of the four known host range genes present in VACV, only SPI-1 and K1L are deleted or truncated in MVA, whereas C7L and E3L are preserved. Deletion of SPI-1 and K1L contributed to the limited MVA host range but their reconstitution only partially reversed the MVA host range restriction in selected cell lines (33,36). Marker rescue experiments using large fragments of the CVA genome indicated that at least two further host range genes apart from SPI-1, C7L and K1L might reside in the left terminal region of the VACV genome (36).

However, while certain studies have indicated that MVA fails to replicate in human cells (7,17,20,32) others have clearly demonstrated that MVA does have a limited ability to replicate in various human cell lines, such as HeLa (5,12,36), 293 (12) and HaCat (6,9). In particular, MVA does not replicate inter alia in the human cell line MRC-5 (ATCC CCL-171).

The replication of several MVA viruses in different human cell types has been compared (31). MVA-I721 (GenBank DQ983236) had a very different replication profile compared to the other two MVA viruses, and most human cell lines were permissive for MVA-I721, which actually had a higher replication in HaCaT, 143B cells than CVA (Id.). Even MVA-572 replicated in the human HaCaT cell line, which was shown to be semi-permissive for this MVA virus (Id.). MVA-BN® was clearly shown to be the most attenuated virus and failed to replicate in any of the human cell lines tested (Id.).

MVA-572 and MVA-I721 (GenBank DQ983236), but not MVA-BN®, killed immune-suppressed mice (Id.). Viruses isolated from dead animals were shown to represent variants present within MVA-572 or MVA-I721 used to inoculate the mice (Id.). These subpopulations were shown to encode mutations, or contain less than the six deletions associated with MVA and had significantly altered phenotypes compared to the parental MVA strains (Id.). Thus, the differences between the replication of these viruses in human cell lines appear to be due to subpopulations of viruses in MVA-575 and MVA-I721, which are not present in MVA-BN®.

A need therefore exists for new attenuated forms of vaccinia virus as well as for methods and compositions for determining the bases of replication of vaccinia viruses in human cells.

The present inventors have cloned both the MVA and the parental CVA genome as bacterial artificial chromosomes (BACs) and have sequentially introduced the six major MVA deletions into the cloned CVA genome. Reconstituted mutant CVA viruses containing up to six major MVA deletions showed no detectable replication restriction in 12 of 14 mammalian cell lines tested; the exceptions were rabbit cell lines RK13 and SIRC. In mice, CVA mutants with up to three deletions showed slightly enhanced virulence, suggesting that gene deletion in replicating vaccinia virus (VACV) can result in gain of fitness in vivo. CVA mutants containing five or all six deletions were still pathogenic, with a moderate degree of attenuation. Deletion V was mainly responsible for the attenuated phenotype of these mutants. In conclusion, though loss or truncation of all 31 open reading frames in the six major deletions was not sufficient to reproduce the specific MVA phenotype of strong attenuation and highly restricted host range, such deleted VACV variants are nevertheless important intermediates in preparing mutated vaccinia virus deletion variants. Such vaccinia virus deletion variants might preferably by host range restricted and preferably avirulent, thereby resembling MVA, in particular, MVA-BN. Indeed, based on the present inventors' observation, mutations in viral genes outside or in association with the six major deletions appear to contribute significantly to a phenotype resembling that of MVA, in particular MVA-BN. In fact, host range restriction and avirulence of MVA are most likely a cooperative effect of gene deletions and mutations involving the major deletions.

To this end, the present invention thus provides, inter alia, such intermediates (i.e., vaccinia virus deletion variants (dVACV)) and mutated vaccinia virus deletion variants (mdVACV) obtainable by introducing one or more mutations into the genome of said intermediates as well as methods for the preparation of dVACVs and mdVACVs. Accordingly, the present invention therefore provides means and methods to facilitate and/or accelerate mutagenesis and thus evolution of VACVs that resemble MVA-BN. Thereby, the present invention provides useful a basis for the identification of genes that are in addition to the well-known six deletions of MVA decisive for the safe but highly immunogenioc MVA vector. Put it differently, the present invention provides the tools for the generation of VACVs that have the same properties as MVA-BN.

Accordingly one aspect of the invention provides a genome of a vaccinia virus deletion variant (dVACV) obtainable by a method comprising:

a) providing a genome of a vaccinia virus (VACV);
b) deleting at least one sequence from the VACV genome, said at least one sequence to be deleted corresponding to a sequence selected from:
  del I (positions 4052-7465 of GenBank AM501482; ECACC 10062901);
  del II (positions 23139-25884 of GenBank AM501482; ECACC 10062901);
  del III (positions 158867-162413 of GenBank AM501482; ECACC 10062901);
  del IV (positions 180639-187092 of GenBank AM501482; ECACC 10062901);
  del V (positions 17438-22159 of GenBank AM501482; ECACC 10062901); and/or
  del VI (positions 135481-139264 of GenBank AM501482; ECACC 10062901), wherein the dVACV is replication competent in at least one human cell line, for example the human cell line MRC-5 (ATCC CCL-171), and wherein the genomes of the following viruses are disclaimed: vP668, vP681, vP749, vP774, vP796, vP811 (25), MVA-I721 (GenBank accession number DQ983236) (1) and VACV strain Tian Tan mutant $MVTT_{2-GFP}$ (39, 40). Also excluded is vP 759 (25).

Such a genome of a vaccinia virus deletion variant (dVACV) is envisaged to be an intermediate for the preparation of a mutated vaccinia virus deletion variant (mdVACV).

A related aspect of the invention provides a vaccinia virus lacking at least one sequence corresponding to del I, del II, del III, del IV, del V and/or del VI as set out above (dVACV), said dVACV being replication competent in at least one human cell line, for example the human cell line MRC-5 (ATCC CCL-171), and wherein the following viruses are disclaimed: vP668, vP681, vP749, vP774, vP796, vP811 (25), MVA-I721 (GenBank accession number DQ983236) (1) and VACV strain Tian Tan mutant $MVTT_{2-GFP}$ (39). Also excluded is vP 759 (25).

The chorioallantois vaccinia virus Ankara containing the sequence indicated in GenBank accession number AM501482 was deposited on Jun. 29, 2010 as "CHORIOALLANTOIS VACCINIA VIRUS ANKARA-PP" (CVA-PP) with the European Collection of Animal Cell Cultures (ECACC), Vaccine Research and Production Laboratory, Public Health Laboratory Service, Centre for Applied Microbiology and Research, Porton Down, Salisbury, Wiltshire SP4 0JG, United Kingdom, and was assigned the accession number 10062901.

As used herein, a "vaccinia virus genome" or "VACV genome" denotes the sequence of a vaccinia virus prior to a respective deletion of del I, del II, del III, del IV, del V and/or del V, and prior to any respective mutation by at least one insertion, deletion, substitution or inversion (as further discussed herein below). A "VACV genome" may therefore be a wild-type VACV sequence with no deletions or mutations of any type relative to the respective strain as it is isolated from nature. Alternatively, the "VACV genome" may also be a sequence which, relative to a particular wild type strain, already contains one or more natural (i.e. accrued in nature) or artificial (i.e. introduced by man) deletion(s) and/or mutation(s), but which is intended to be used as a starting material for introducing further deletions and/or mutations according to the present invention.

As used herein, a "deletion variant of a vaccinia virus genome" or "dVACV genome" denotes the sequence of a vaccinia virus from which a sequence corresponding to at least one of del I, del II, del III, del IV, del V and/or del VI is deleted. The sequences of del I, del II, del III, del IV, del V and/or del VI are uniquely identified by reference to the complete coding region of the CVA isolate registered in the GenBank database under accession number AM501482, and physically deposited with the ECACC under the accession number 10062901. A preferred deletion variant of a vaccinia virus is a chorioallantois vaccinia virus (CVA) deletion variant as described herein.

GenBank database accession number AM501482 when referred to herein includes the version AM501482.1 of AM501482 of Nov. 21, 2007 as well as the version of AM501482.1 of Jan. 31, 2009. The sequence of both versions is, to the best of applicant's knowledge, identical. However, in case of doubt, the version of Nov. 21, 2007 is preferred. Said sequence is also disclosed in Meisinger-Henschel et al. (29).

Nucleotide positions 4052-7465 of this sequence correspond to del I. Nucleotide positions 23139-25884 of this sequence correspond to del II. Nucleotide positions 158867-162413 of this sequence correspond to del III. Nucleotide positions 180639-187092 of this sequence correspond to del IV. Nucleotide positions 17438-22159 of this sequence correspond to del V. Nucleotide positions 135481-139264 of this sequence correspond to del VI. These sequence regions of GenBank accession number AM501482 are also set out in Meisinger-Henschel et al. (2007). J. Gen. Virol. 88, 3249-3259 (see FIG. 2B on page 3252 thereof) and correspond to 6 regions of the CVA genome which are missing in MVA.

As used herein, the term "vaccinia virus", abbreviated as "VACV" includes preferably a chorioallantois virus, abbreviated as CVA. Accordingly, the term "deletion variant of a vaccinia virus", abbreviated as "dVACV" includes a dCVA. Similarly, the term "mutated deletion variant of a vaccinia virus", abbreviated as "mdVACV" includes a "mdCVA".

As used herein, a sequence "corresponding to" a specified portion of GenBank accession number AM501482 (corresponding to the genome of the virus "CVA-PP" deposited with the ECACC under accession number 10062901) refers to a sequence stretch which, when a sequence in question is aligned with AM501482 by standard methods, exhibits significant homology to the indicated portion or portions of AM501482. Different strains of VACV may contain sequences which, while similar to del I-del VI in GenBank accession number AM501482, are not identical to these sequences and in particular may contain different, fewer or more nucleotides than the reference sequence. The stretches of a sequence in question which are similar to del I-del VI in GenBank AM501482 can be easily determined by standard in silico alignment techniques using established software for example using Clustal W version 2, with parameters set to "standard" or "preset". Clustal W version 2 may be used and/or obtained online at the following address: http://www.ebi.ac.uk/Tools/clustalw2/index.html. For example, a sequence which is not identical to any of del I-del VI, but nevertheless will be understood as "corresponding to" any of these sequences in the sense of the present invention may bear at least 70% identity, preferably at least 75% identity, more preferably at least 80% identity, most preferably at least 90% identity to one or more of the partial sequences of AM501482 designated del I-del VI. Thus, sequences "corresponding to" del I-del VI include, but are not limited to the specific sequences indicated above with reference to the sequence given by GenBank accession number AM501482.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or" as used herein.

As used herein, "replication competent" refers to the ability of a virus to replicate in a given cell, for example in a given human cell line, such as for example the cell line MRC-5 indicated above. A virus which can replicate in the specified cell is denoted "replication competent" whereas a virus which is not able to replicate in such a cell is referred to as "replication incompetent". A replication competent virus is thus sometimes described as being able to "replicate" or to "reproductively replicate" under the test conditions of choice. The growth behavior or amplification/replication of a virus may be expressed by the ratio of virus produced by an infected cell ("output titer") to the amount initially used to infect the cell ("input titer"). The ratio of output:input is the "amplification ratio", and this amplification ratio provides the desired measure of replication competence or incompetence.

The amplification ratio can also be used as a quantitative measure of replication competence. As used herein, a virus which is "replication restricted" or "replication attenuated" refers to a partially or wholly impaired ability of a virus in question to replicate under given conditions, as compared to the corresponding ability of a reference virus to replicate under the same conditions. In in vitro settings (e.g. cell lines) the virus in question is referred to as "replication restricted". In in vivo settings (e.g. in animals) the virus in question is referred to as "replication attenuated". These terms are used accordingly herein. The restriction or attenuation of replication competence (depending on whether the setting is in vitro or in vivo, respectively) may decrease the amplification ratio such that it is still 1.0 or above, or the amplification ratio may be decreased to a value below 1.0. In the former case, the virus still remains replication competent than its reference virus under equivalent conditions, although less so. In the latter case, the virus in question is "replication incompetent". As such, a virus which is "replication restricted" or "replication attenuated" need not necessarily be "replication incompetent".

An amplification ratio of 1.0 defines a replication status wherein the amount of virus produced from the infected cells is the same as the amount initially used to infect the cell, indicating that replication has taken place; an amplification ratio of 1.0 means that a respective virus is "replication competent" in the infected cell. The same holds for an amplification ratio of >1; a virus giving rise to an amplification ratio of >1 indicates replication competence of the virus in that particular cell. On the other hand, an amplification ratio of <1 indicates a decrease of output titer below input titer, a lack of reproductive replication in the cell, and thus replication incompetence. The respective degree of amplification competence or incompetence of a particular virus in a particular cell will depend on how much higher or lower than 1.0 the measured amplification ratio is. However, as long as the amplification ratio is greater than or equal to 1.0 in a cell of choice, one may speak qualitatively of a "replication competent" virus in the sense of the present invention, while a "replication incompetent" virus in the sense of the present invention is qualitatively associated with an amplification ratio of less than 1.0.

The amplification ratio of a given virus (including the constructs of the present invention) in a given cell may be measured in the following way, commonly known to the skilled person:

Generally, in order to determine whether a given virus is replication-competent or replication-defective, the respective cell type/s of choice is/are infected with a known amount of the test virus, representing the "input" titer. The input titers are determined prior to assessment of replication properties using permissive cells for the titration of input virus by the $TCID_{50}$ method (14,27). Virus inocula are diluted appropriately to obtain the desired input titer. Infections of the cell types of choice are left for a total of 4 days, after which time viral samples are prepared by lysis of the infected cells. These virus samples are then titrated on CEF indicator cells as described below. This is the "output" titer. A ratio of output to input titer below 1 indicates that the test virus is replication incompetent under the test conditions, whereas a ratio of output to input titer which is equal to or greater than 1 indicates that the test virus is replication competent under the test conditions (see above).

To determine the replication properties of a test virus, cells of choice are seeded into 6-well-plates at a concentration of $5\times10^5$ cells/well and incubated over night at 37 C, 5% $CO_2$ in DMEM (Gibco, Cat. No. 61965-026) plus 2% FCS. Cell culture medium is removed and cells are incubated with the virus inoculum for one hour at 37° C., 5% $CO_2$ atmosphere. The amount of virus used for each infection of the different cell types is $5\times10^4$ $TCID_{50}$ This is the "Input" titer of virus referred to above. After one hour at 37° C., the inoculum is removed by aspiration and cells are then washed 3 times with DMEM and finally 1 ml DMEM, 2% FCS is added, and the plates are left to incubate for 96 hours (4 days) at 37° C., 5% $CO_2$. The infections are stopped by freezing the plates at −80° C. ready for titration analysis. The resulting cell lysate comprising the remainders of the infected cells and the incubation medium is the virus sample to be titrated for determination of the output titer. Thus, the sample contains intracellular as well as extracellular virus.

Titration analysis of virus samples from replication analyses (immunostaining with a vaccinia virus-specific antibody): For titration of viral output titer, CEF cells are seeded on 96-well-plates in RPMI (Gibco, Cat. No. 61870-010), 7% FCS, 1% Antibiotic/Antimycotic (Gibco, Cat. No. 15240-062) at a concentration of $1\times10^4$ cells/well and incubated over night at 37° C., 5% $CO_2$. The 6-well plates containing the infection experiments are frozen/thawed 3 times and dilutions of $10^{-1}$ to $10^{-12}$ are prepared using RPMI growth medium. Virus dilutions are distributed onto test cells in replicates of 8 and incubated for five days at 37° C., 5% $CO_2$ to allow virus replication. Test cells are fixed (acetone/methanol 1:1) for 10 min, air-dried, washed once with washing buffer (PBS/0.05% Tween20) and incubated with polyclonal vaccinia virus-specific antibody (e.g. Quartett Berlin, Cat. No. 9503-2057) at a 1:1000 dilution in incubation buffer (PBS/3% FCS) for one hour at RT. After washing twice with washing buffer the horseradish peroxidase (HRP)-coupled secondary anti-rabbit IgG antibody (Promega Mannheim, Cat. No. W4011) is added at a 1:1000 dilution in incubation buffer for one hour at RT. Cells are again washed twice with washing buffer and incubated with staining solution (3,3', 5,5' tetramethyl-benzidine chromogenic substrate (1.2 mM; Seramun Diagnostic GmbH, Catalogue number S-002-5-TMB/) diluted 1:2 with PBS) for 15 min at RT. Plates are washed once with washing buffer. Using a microscope, the plates are scored for infected cells which appear purple (Refer to Appendix 3 for scoring sheets).

Every well showing purple staining is marked as positive for viral replication and the titer is calculated using the Spearman-Kaerber method ($TCID_{50}$ assay)(14,27) This is the "Output" titer.

With values now obtained for both Input and Output titers, the amplification ratio of Output:Input may be calculated as indicative of the extent of replication of a given virus in a given cell type. Using the above procedure, it is easily determined whether, and to what extent, a particular virus, is replication competent in the cell line of choice, e.g. human MRC-5 cells.

The dVACV results from deleting one or more sequences corresponding to del I, del II, del III, del IV, del V and/or del VI as defined herein above. All possible combinations of deletion of sequences corresponding to del I-del VI are specifically encompassed by this invention, for example, sequences corresponding to del III alone, del II with del IV, del I with del V and del VI, etc. In this way, the dVACV can have 1, 2, 3, 4, 5 or 6 deletions of sequences corresponding to del I, del II, del III, del IV, del V and/or del VI as defined herein above. Preferably, the dVACV is the result of deleting sequences corresponding to all six of del I, del II, del III, del IV, del V and del VI as defined herein above with reference to GenBank accession number AM501482.

The dVACV, for example dCVA, is replication competent in a human cell line, for example in a selected from 293, 143B and MRC-5 cell lines. It is preferred that the dVACV is replication competent in the human cell line MRC-5 in the sense set out above. The dVACV, for example dCVA, is preferably replication competent in the cell line, preferably in a human cell line as described herein, e.g. in the human cell line MRC-5, such that it exhibits an amplification ratio of greater than 5, 10, 20, 50, 100, 250, 500 or 1000 measured as set out above.

As mentioned above, it is known that sequences corresponding to del I through del VI were lost from the CVA genome in the many passages of the parental CVA virus en route to MVA. MVA is exceptionally suitable for use in viral-based vaccination regimens because it functions as a source of the antigen associated with the disease to be vaccinated against, while it does not lead to cytopathic effects in the cells of human hosts to which it is administered. In studies of the genetic relationship between CVA and MVA, the present inventors have surprisingly found that the deletion of sequences corresponding to del I through del VI in CVA is in itself not enough to confer the advantageous characteristics upon which the use of MVA as a vector in viral-based vaccination regimens depends. The advantageous attenuation of MVA appears to be due to a combination of (a) deletion of the sequences del I through del VI and (b) accrual of other mutations going beyond the deletion of these sequences. In providing a vaccinia virus deletion variant (dVACV) from which at least one sequence corresponding to del I-del VI has been deleted, the present invention advantageously provides a vital tool which can be used as a starting point for effecting further mutations going beyond the deletions mentioned above. The dVACV genome and vector, especially virus, constructs of the present invention thus provide an important means for determining the basis of attenuation of viral replication so important for a successful viral-based vaccine, ultimately aiding in the development of alternate viral vectors useful in viral-based vaccination regimens.

In an especially preferred embodiment of various aspects of the present invention, the dVACV is a dCVA. It is especially preferred that the dCVA is derived from CVA having a genomic sequence as set out under GenBank accession number AM501482. The corresponding physical virus is deposited as the strain "CVA-PP" with the ECACC under accession number 10062901.

One preferred dCVA genome comprises a genome lacking a sequence corresponding to del V, more preferred lacking sequences corresponding to del I and IV, more preferred lacking sequences corresponding to del I, II and IV, even more preferred lacking sequences corresponding to del I, II, III, and IV, still more preferred lacking sequences corresponding to del I, II, III, IV and V, and most preferred lacking sequences corresponding to del I, II, III, IV, V and VI.

Accordingly, in a preferred embodiment, the method by which the vaccinia virus variant is obtainable further comprises introducing at least one mutation into the dVACV genome to yield a mutated vaccinia virus deletion variant (mdVACV), wherein the mdVACV is replication competent in at least one human cell line and wherein the replication competence of the mdVACV in the human cell line is restricted relative to the replication competence of dVACV in the human cell line. The human cell line may for example be MRC-5 (ATCC CCL-171).

A related preferred embodiment provides a dVACV additionally comprising at least one mutation (mdVACV), wherein the mdVACV is replication competent in at least one human cell line and wherein the replication competence of the mdVACV in the human cell line is restricted relative to the replication competence of dVACV the human cell line. The human cell line may for example be MRC-5 (ATCC CCL-171).

As explained above, the genome of a mutated deletion variant which is restricted or attenuated in its replication competence relative to its progenitor dVACV can provide useful information as to the types of genomic mutations responsible for the a desired restriction of replication competence under specified conditions. Known viruses, such as wild-type vaccinia viruses present difficulties for use as a viral-based vaccine; while they may elicit a desired immunogenic response to an antigen of interest, they are also often virulent enough to result in significant pathogenicity and morbidity upon administration, and may therefore be unsafe to administer to patients. In contrast, the mutated vaccinia virus deletions variants (mdVACV) of the present embodiment are restricted in their replication relative to their parent dVACV and therefore have reduced pathogenicity while retaining their ability to act as a delivery agent for the coding sequence of an antigen of interest in a vaccination regimen. Although mdVACV genomes according to this embodiment of the invention remain replication competent, a restriction of this replication competence relative to the corresponding dVACV parent can provide valuable information as to the types and locations of mutations responsible for reduction and ultimate loss of replicative capacity. This information is important in the further design of replication attenuated viruses for use in virus-based vaccination regimens.

A "mutation" as used herein is to be understood as at least one nucleotide insertion, deletion, substitution (including a transition and a transversion) or inversion in a persisting region of the sequence. In the case that the mutation leading to the mdVACV is or includes a deletion, it is preferred that the "deletion" removes at least one nucleotide from a region other than a region corresponding to del I-del VI as defined above. As such, the when the mutation leading to mdVACV from dVACV is a deletion, it is preferred that this deletion be a deletion of a sequence (at least one nucleotide) other than sequences corresponding to any of del I-del VI remaining after conversion of VACV to dVACV. A "persisting region" refers in VACV to a region which will not be deleted in the final construct, and in dVACV to a region of the genome remaining following deletion of one or more of del I-del VI. Thus, a persisting region is a region within the VACV genome which will remain in mdVACV after all deletions to be effected have been effected, regardless of whether such deletions are of one or more of del I-del VI, or in another region not corresponding to del I-del VI. The at least one mutation may be introduced into this region by commonly known methods, e.g. targeted mutagenesis, error-prone PCR, etc.

The mdVACV genome set out above according to this embodiment of the invention, when in an mdVACV, is restricted in its replication in a human cell line, e.g. in the human cell line MRC-5 as compared to the corresponding dVACV parent and/or is attenuated in its pathogenicity in an animal as compared to the corresponding dVACV parent. Suitable methods for determining restriction of replication competence of a virus are set out above. Suitable methods for determining attenuation the replication competence of a virus in an animal, as well as for determining the pathogenicity and/or immunogenicity in an animal are set out below.

The order in which the at least one deletion and at least one mutation are introduced is not crucial. That is, it is possible to generate the mdVACV by first deleting at least one sequence corresponding to del I-del VI (as defined herein above) from the VACV genome to yield a dVACV and then introducing at least one mutation in a persisting region to yield a final mdVACV. Alternatively, it is possible to first introduce at least one mutation in a region one intends to be a persisting region, and then to delete at least one sequence corresponding to del I-del VI, once again yielding the final mdVACV. However, as will become apparent below, it can be advantageous to first delete sequences to yield dVACV and then introduce one or more further mutations to yield the final mdVACV, since it is then possible to establish, in a controlled stepwise manner, the relevance of additional mutations in dVACV for the final desired attenuation of the mdVACV product (genome or virus). As explained above, this is part of the advantage of the present invention, as it allows the genetic basis of an advantageous restriction in vitro and corresponding ultimate attenuation in vivo of viral replicative capacity to be better understood, established and then finally exploited in the generation of new viral constructs suitable for use in viral-based vaccination regimens.

The dVACV, preferably the dCVA, can comprise additional mutations beyond the deletion of at least one of del I-del VI and, with such additional mutation(s) in persisting regions, is designated mdVACV. In the preferable case that dVACV is dCVA, the corresponding mdVACV is mdCVA. The skilled artisan understands that there exist a multitude of mutations that can be made using molecular biological or genetic techniques to alter the nucleotide sequence of the dVACV, preferably dCVA. The skilled artisan is further aware that a multitude of mutations can be made without disturbing the ability of the dVACV to replicate in a human cell line, for example, conservative and silent mutations, as well as mutations in non-coding regions. However, it is preferred to introduce the at least one mutation into a coding region.

In one embodiment of the invention, the replication competence of an mdVACV comprising additional mutations relative to dVACV is assayed in a human cell line to see whether the additional mutations going beyond the deletions in dVACV restrict replication competence of the mdVACV genome in the human cell line used for the assay. This can be performed as set out above, and one would conclude a restricted replication competence in mdVACV relative to a parent dVACV in the case that the amplification ratio as defined above were lower for mdVACV than for dVACV in the same human cell line. This replication-restricted mdVACV can then be used as a tool for a further round of optimization by introducing further mutations and then reassessing the replication competence, either with respect to dVACV or with respect to mdVACV. Thus, the generation of a replication-restricted virus of increased suitability for use in a viral-based vaccination regimen can be effected in an iterative manner in which additional incorporated mutations bring about an additional restriction of replication competence in a given human cell line. That is, the mdVACV at the end of one round of optimization becomes the dVACV at the start of a further round of optimization to yield yet a further mdVACV which is restricted even further than the first. Suitable cell lines include 143B (ATCC CRL-8303, 293 (ATCC CRL-1573), HaCaT (6), Hela (ATCC CCL-2), MRC-5 (ATCC CCL-171), BS-C-1 (ATCC CCL-26), CV-1 (ATCC CCL-70), BALB/3T12-3 (ATCC CCL-164), MDCK (ATCC CCL-34), RK-13 (ATCC CCL-37), SIRC (ATCC CCL-60) and IEC-6 (ATCC CRL-1592). The human cell line MRC-5 (ATCC CCL-171) is especially preferred. In a preferred embodiment, it is determined whether the mutation of dVACV, preferably of dCVA, affects the replication of the resulting mdVACV, preferably mdCVA, in a human cell line, preferably in MRC-5 (ATCC CCL-171).

By incorporating mutations, optionally in an iterative manner, into dVACV to create one or more types of mdVACV, it is possible to restrict the replication competence of mdVACV in a human cell line to such an extent that replication competence in this human cell line is lost altogether. This corresponds to the case in which the amplification ratio measured upon infecting a human cell line of choice with mdVACV is below 1.0, preferably well below 1.0, meaning that less virus is measured following infection than was used to initially infect the cells. In this case, viral infection with a replication incompetent mdVACV proceeds with an overall loss of mdVACV. Such mdVACV genomes and vectors, especially virus vectors, are especially advantageous in viral-based vaccination strategies, since they have the potential to elicit the desired immunogenic response without any replication or pathogenicity.

Accordingly, a further aspect of the invention provides a genome of a mutated vaccinia virus deletion variant (mdVACV), obtainable by a method comprising:

a) providing a genome of a vaccinia virus (VACV);
b) deleting at least one sequence corresponding to del I, del II, del III, del IV, del V and/or del VI as set out above; and
c) introducing at least one mutation into the VACV genome, wherein the mdVACV is replication incompetent in at least one human cell line, for example the human cell line MRC-5 (ATCC CCL-171), and wherein the genomes of the following viruses are disclaimed: MVA-572 (ECACC V94012707), MVA-BN® (GenBank accession number DQ983238), MVA II/85 (5), MVA (ATCC VR-1508), and NYVAC (34). Also excluded is Acambis 3000 modified Virus Ankara, the sequence of which is deposited with GenBank under accession number AY603355 and MVA-I721 (1).

A related aspect of the invention provides a mutated vaccinia virus deletion variant (mdVACV), wherein said mdVACV lacks at least one sequence corresponding to del I, del II, del III, del IV, del V and/or del VI as set out above, wherein said mdVACV comprises at least one mutation, wherein the mdVACV is replication incompetent in at least one human cell line, for example the human cell line MRC-5 (ATCC CCL-171), and wherein the following viruses are disclaimed: MVA-572 (ECACC V94012707), MVA-BN® (GenBank accession number DQ983238), MVA II/85 (5), MVA ATCC VR-1508, and NYVAC (34). Also excluded is Acambis 3000 modified Virus Ankara, the sequence of which is deposited with GenBank under accession number AY603355 and MVA-I721 (1).

Preferably, a mdVACV or mdCVA obtainable by the methods described herein has the same properties/features as MVA-BN (deposited with ECACC as V00083008). These properties are: capability to reproductive replication in chicken embryo fibroblasts (CEF), no capability of reproductive replication in the human keratinocyte cell line HaCat, the human bone osteosarcoma cell line 143B, and the human cervix adenocarcinoma cell line HeLa.

These features of MVA-BN, the description of biological assays allowing to evaluate whether a MVA strain is MVA-BN as well as methods allowing to obtain MVA-BN (or a derivative thereof) are disclosed in detail in WO 02/42480 and WO 03048184. The content of this application is included in the present application by reference. Said reference also discloses how MVA and other vaccinia viruses can be propagated.

Given the above, the present invention contemplates a mdVACV, preferably a mdCVA which has the same properties as MVA-BN, whereby the following viruses/genomes are not encompassed: MVA-572 (ECACC V94012707), MVA-BN, MVA II/85, MVA ATCC VR-1508 and NYVAC. Also not encompassed is Acambis 3000 modified Virus Ankara, the sequence of which is deposied with GenBank under accession number AY603355 and MVA-I721.

An dVACV, preferably dCVA, or mdVACV, preferably mdCVA of the present invention is envisaged to be comprised in a pharmaceutical or diagnostic composition. It may also be comprised in a vaccine composition.

In providing an mdVACV lacking at least one sequence corresponding to del I-del VI and comprising at least one mutation in the remaining, persisting regions, the inventors have advantageously provided a path to modify vaccinia virus variants of potentially high suitability for use as viral vectors and viral-vaccination regimens.

As mentioned above, not all of the sequences corresponding to del I-del VI need be absent in the dVACV or mdVACV construct. However, it may be preferable to remove all of del I-del VI, so that dVACV and/or mdVACV contains no sequences corresponding to these.

With regard to the at least one mutation in mdVACV, it is preferred that the mutation is introduced into at least one coding region of the VACV genome. For example, the set coding region may be selected from F5L, B8R, B19R, A31R, A36R, A37R, and A4L. Mutations in one or more of these coding regions are preferred. These coding regions are defined for the published sequence of VACV strain Copenhagen (GenBank accession number M35027).

The VACV genome is preferably chorioallantois vaccinia virus Ankara (CVA), preferably CVA, the genome sequence of which is indicated under GeneBank accession number AM501482. The CVA containing the sequence indicated in GenBank accession number AM501482 is deposited as “CVA-PP” with the ECACC under the accession number 10062901.

The mdVACV variant according to the present invention has decisive advantages over other VACV. Known viruses, such as wild-type vaccinia viruses such as CVA, may present difficulties for use as a viral-based vaccine; while they may elicit a desired immunogenic response to an antigen of interest, they may be virulent enough to result in significant pathogenicity and morbidity upon administration, and may therefore be unsafe to administer to patients. In contrast, the mdVACV variants of the present invention are attenuated in their in vitro and/or in vivo replication competence and/or their in vivo pathogenicity and/or their in vivo immunogenicity while retaining their ability to act as a delivery agent for the coding sequence of an antigen of interest as part of a vaccination regimen. They are therefore much safer to use than many existing viruses. Thus, the present invention advantageously extends access to new viral genomes and new viruses which, like MVA, combine the advantages of high immunogenicity and good safety profiles in mammalian, for example human, subjects.

A further aspect of the invention relates to a vector, preferably a DNA vector comprising a dVACV (specifically the genome of a dVACV) or an mdVACV genome as set out above. Another aspect of the invention is a DNA vector comprising the genome of a dCVA which is obtainable by a method of preparing a dVACV as described in detail below. Preferably, said dCVA or said DNA vector comprising the genome of said dCVA reproductively replicates with an amplification ratio greater than 5 in the human 293 cell line, human 143B cell line or human MRC-5 cell line. The vector may for example advantageously be a bacterial artificial chromosome (BAC), a plasmid or a virus. In the case that the vector is a virus, it is especially preferred that the virus is a vaccinia virus. As such, the present invention also provides a vaccinia virus comprising a genome as set out herein above.

The vector, preferably DNA vector comprising a deletion variant of the VACV genome (dVACV genome), preferably a deletion variant of the CVA genome (dCVA genome), can be any vector with the capacity for a DNA molecule as large as that of the dVACV genome, preferably the dCVA genome. In a preferred embodiment, the DNA vector is a bacterial artificial chromosome (BAC), P-1 derived artificial chromosome (PAC), yeast artificial chromosome (YAC), mammalian artificial chromosome (MAC) or human artificial chromosome (HAC) (Harrington et al. 1997. Nature Genetics 15:345; Takahashi et al. 2010. Methods Mol. Biol. 597:93; Giraldo et al. 2001. Transgenetic Res. 10:83; Amemiya et al. 1991. Methods Cell Biol. 60:235; Bunnell et al. 2005. Expert Opin. Biol. Ther. 5:195). Most preferably, the DNA vector is a bacterial artificial chromosome (BAC). In the event a DNA vector is used, infectious virus can be generated from the DNA vectors using routine techniques in the art, for example, as described in the Example herein below. In one embodiment, dCVA virus (as an illustrative example of dVACV) can be produced form a vector comprising the genome of a dCVA using Shope fibroma virus (SFV) as helper virus (47). In another embodiment, a helper cell line can be used to provide the transcription system encoded by poxviruses to generate authentic viral genomes from the transfected vector that are packaged into infectious progeny virus.

After vector transfection and SFV infection of BHK-21 cells, infectious dVACV, preferably infectious dCVA, can be rescued. To remove the helper virus, three passages on CEF cells or another cell type which is non-permissive for SFV can be performed. PCR can be used to confirm that no SFV DNA and thus no infectious SFV is present in stocks of rescued virus after three passages in CEF cells.

A further aspect of the invention provides an isolated cell comprising the genome of any of the above or below dVACV or mdVACV, any vector as set out above, or a dVACV or mdVACV as set above. The isolated cell is preferably a yeast cell, a bacterial cell or a mammalian cell. In the event that the cell is a mammalian cell it is preferable that the mammalian cell is a mouse cell, a monkey cell or a rabbit cell. In especially preferred embodiments, the cell is selected from CEF, BHK-21, 143B, 293, HaCat, Hela, MRC-5, BS-C-1, CV-1, Vero BALB/3T12-3, MDCK, RK-13, SIRC or IEC-6 cell. Most preferred are MRC-5 cells.

As is apparent from the foregoing, generation of an mdVACV variant represents an advantageous way of arriving at alternative viral vectors which may be used to deliver a desired antigen to a host or host cell without causing cytopathic effects in the host or host cell, thus opening the path to alternative virus-based vaccination strategies. Accordingly, a further aspect of the invention provides a method for determining the effect of a mutation on a vaccinia virus (VACV) comprising:

(a) providing a vector comprising the genome of a VACV from which at least one sequence corresponding to a sequence selected from
  - del I (positions 4052-7465 of GenBank AM501482; ECACC 10062901);
  - del II (positions 23139-25884 of GenBank AM501482; ECACC 10062901);
  - del III (positions 158867-162413 of GenBank AM501482; ECACC 10062901);
  - del IV (positions 180639-187092 of GenBank AM501482; ECACC 10062901);
  - del V (positions 17438-22159 of GenBank AM501482; ECACC 10062901); and/or
  - del VI (positions 135481-139264 of GenBank AM501482; ECACC 10062901) is deleted, wherein the deleted VACV genome replicates in a human cell line;

(b) introducing at least one mutation into the dVACV genome; and (c) determining whether the mutation affects the replication of the mutated Vaccinia virus deletion variant (mdVACV).

In a preferred aspect, said method for determining the effect of a mutation on a VACV further comprises
- measuring the amplification ratio of said dVACV in a human cell line; and/or
- measuring the amplification ratio of mdVACV in said human cell line.

In another preferred aspect, said method further comprises comparing the amplification ratio of said dVACV with the amplification ratio of said mdVACV in order to determine whether the at least one mutation affects the replication of said mdVACV in said human cell line.

In the above method, the amplification ratios of dVACV and mdVACV in the same human cell line (termed first and second replications, respectively) can be measured in the manner set out hereinabove. "Measuring the amplification ratio" when used herein also includes determining the amplification ratio. Simple numerical comparison of the first and second replications for dVACV and mdVACV, respectively, then serves as the desired indication of whether or not a given mutation added to a dVACV affected the replication of the mdVACV as compared to dVACV. Specifically, if the "first replication" measured for dVACV is greater than the "second replication" measured for mdVACV, this indicates that a mutation introduced into dVACV to yield mdVACV restricted the replication competence of the mdVACV relative to the dVACV in the cell used for measurement.

The method according to this aspect of the invention advantageously allows the determination of what sorts of mutations, made in addition to the above specified deletion of at least one sequence corresponding to del I-del VI, will result in a viral vector with an improved or acceptable safety profile, possibly allowing it to be used as part of a viral-based vaccination regimen. This approach of introducing mutations in a controlled, stepwise manner into the genome of a dVACV allows a systematic determination of the types of mutations which result in a virus sufficiently restricted in its replication and/or attenuated in its pathogenicity to be safe for administration to patients. For instance, in the event that the magnitude of the first replication is greater than that of the second replication, then one may conclude by this comparison that a mutation yielded a mdVACV which will not replicate as well as, and is therefore safer than, its parent virus dVACV. On the other hand, if the magnitude of the first replication is comparable to that of the second replication, or is even less than it, then one may conclude that the additional mutation in the mdVACV either had no effect on safety, or even rendered mdVACV more unsuitable for use as a viral vaccine than its parent virus. Performing the method according to this aspect of the invention in an iterative manner allows one to identify and optimize genomic mutations in dVACV variants which move closer to, or result in viral phenotypes suitable for use in viral-based vaccination regimens.

As mentioned above, the method according to this aspect of the invention may advantageously be used in an iterative manner. That is, having established that a particular mutation or set of mutations renders an mdVACV less replicative and therefore safer than its predecessor dVACV, one can then further improve the resulting mdVACV by introducing further mutations into persisting sequences in it. Thus, the mdVACV of one round of modification by mutation may become the dVACV of a respective subsequent round. Besides the advantage of continual improvement in the desired safety characteristics of vaccinia virus variants for potential use in viral-based vaccine strategies, such systematic application of the method according to this aspect of the invention allows the advantageous development of useful systematic rules as to which regions of the VACV genome are best mutated, and as to what the mutation(s) should be, in order to result in the desired attenuation and, thus, safe utility in viral-based vaccination regimes.

Preferably, the human cell line used in the method according to this aspect of the invention is chosen from the human cell line 293 (ATCC CRL-1573), the human cell line 143B (ATCC CRL-8303) and the human cell line MRC-5 (ATCC CCL-171).

Preferably, the dVACV reproductively replicates with an amplification ratio of 10 or greater in the human cell line. This provides a sufficiently high starting value from which restriction of replication capacity due to subsequently introduced mutations may be unambiguously observed and attributed to such mutations.

In further embodiments, the method set out above may further comprise determining whether the mutation affects the replication, pathogenicity and/or immunogenicity of the dVACV in an animal.

To determine these parameters, BALB/c mice may serve as a suitable animal model. These mice can for example be intranasally infected with the test virus.

With regard to in vivo replication, lungs and other organs of intranasally infected mice can for example be analyzed for viral load by measuring the viral titers in organ homogenates as described above using the $TCID_{50}$ method (14,27).

With regard to pathogenicity, this can be measured by using sufficiently high inocula to determine survival after infection. Furthermore, pathogenicity after low and high dose infection can be determined by quantitating body weight loss and signs of disease according to a defined scoring system. Experimental details for determination of pathogenicity of dVACV or mdVACV in BALB/c mice are given in the example below.

With regard to the replication of an mdVACV in an animal, this can be determined in a suitable mouse model. For example, the respective mice can be incapable of producing mature B and T cells. An example of such mice is the transgenic mouse model RAG (can be obtained from Charles River Laboratories) or any other mouse strain can be used that fulfills the requirement of being incapable of producing mature B and T cells, and as such, is severely immunocompromised and highly susceptible to a replicating virus.

In particular, the viruses of the present invention may not kill RAG mice within a time period of at least 45 days, more preferably within at least 60 days, and most preferably within 90 days post infection of the mice with $10^7$ $TCID_{50}$, more preferably with $10^8$ $TCID_{50}$ of virus administered via intraperitoneal injection. The viruses that exhibit "failure to replicate in vivo" are further characterized in that no virus can be recovered from organs or tissues of the RAG mice at the earliest 45 days after infection of the mice with $10^7$ or $10^8$ $TCID_{50}$ of virus administered via intra-peritoneal injection. Measurements are typically made after 60 or 90 days post infection. Detailed information regarding the infection assays using immuno-suppressed mice and the assays used to determine whether virus can be recovered from organs and tissues of infected mice are set out in U.S. Pat. No. 7,384,644. Specifically, mice are infected with an infectious dose of mdVACV of $10^7$ $TCID_{50}$, more preferably with an infectious dose of $10^8$ $TCID_{50}$ via the intraperitoneal route. The inoculum is diluted in PBS and a maximum volume of 500 μl per mouse is applied, preferably a volume of 200 μl per mouse. Mice are visually inspected and checked for signs of disease such as ruffled fur, hunched posture, reduced activity and mobility, gait abnormality, respiratory distress and skin lesions.

After mice have been sacrificed, organs including lung, spleen, liver, ovaries or testes, kidney, brain and intestine are removed using aseptic techniques and stored on ice during the procedure of organ removal. Organs are then frozen at −20° C. until further use. For the titration of viral titers in recovered organs, the organs are thawed by flicking onto a metal wire mesh in 5 ml DMEM in a petri culture dish and pressed through the wire mesh using a syringe plunger until the tissue is homogenized. Any other accepted method to homogenize tissue samples may alternatively be used. The 5 ml of tissue homogenate are collected and either freeze-thawed or sonicated in a Branson Cuphorn sonifier for at least 2 min at 4° C. at 50% maximal power to lyse cells and release viral particles. After sonication, tissue homogenates may be frozen at −20° C. or −80° C. again, or may be immediately used to determine viral titers by the $TCID_{50}$ method as described hereinabove (under the heading "Titration analysis of virus samples from replication analyses") and in the example below (section "Viral replication analysis") and the results are calculated according to the methods of the prior art (14,27). In case homogenates are re-frozen or were prepared by repeated freeze-thawing, samples must be sonicated at least 1 min at 4° C. and 50% maximal power before being used in titration or replication assays.

Titration by the $TCID_{50}$ method (14,27) is performed using replicates of 8 per sample as set out above. Titers are calculated as total viral titer per organ taking into account the volume of the respective tissue homogenate.

Following infection of separate animals with known amounts of dVACV and a given mdVACV, one can compare the relative amounts of dVACV and mdVACV in these animals after a given amount of time. If more dVACV than mdVACV is observed, then one can conclude that the mutation of dVACV advantageously reduced the replicative competence of dVACV. Such an mdVACV may then form the basis, possibly following further optimization by further mutation, of a virus-based vaccination strategy. If on the other hand more mdVACV than dVACV is found in the animals after the given amount of time, then one can conclude that the mutation of dVACV did not reduce the replicative competence of dVACV, indicating that the mutations incorporated should not be carried forward in further optimization to an mdVACV suitable for use in a virus-based vaccination strategy.

With regard to the assessment of in vivo pathogenicity of an mdVACV in question, this can be assessed by measuring body weights before and continuously after infection as a measure of disease as well as body temperature and disease symptoms, according to an arbitrarily defined score. This is set out in greater detail in the example herein below.

With regard to the assessment of immunogenicity of an mdVACV in question, a virus strain can be examined for its ability to induce an immune response using the techniques set out in the examples herein below. Generally, however, the immunogenicity of dVACV and mdVACV can be assessed by analysis of the humoral and cellular immune response against the respective dVACV or mdVACV.

For analysis of humoral immune responses, mice are immunized with $10^7$ $TCID_{50}$ of dVACV and mdVACV by the route of choice (intramuscular, subcutaneous, intraperitoneal or intravenous) for one, two or three times as desired and blood is taken two weeks after each immunization. The dVACV- or mdVACV-specific antibody levels in sera of infected mice can be determined by ELISA as follows: 96-well TRANSP MAXIS plates (Nunc, Wiesbaden, Germany) are coated overnight at 4° C. with 100 μl (7.5 μg/ml) of corresponding viral antigen (i.e. dVACV or mdVACV, as the case may be, or crude extracts of cells infected therewith) in coating buffer (200 mM $Na_2CO_3$, pH 9.6). Alternatively, the virus antigen may be MVA antigen, e.g. a crude extract of MVA infected CEF cells, because MVA will normally be antigenicly highly similar to other vaccinia strains. Plates are blocked with 200 μl of PBS-FCS 5% (PAA Laboratories, Linz, Austria) for 30 min at room temperature. Plates are washed and two-fold serial dilutions of mouse test sera are incubated for 1 h at room temperature (RT). If necessary (i.e. if titers are above 1:2000), pre-dilutions of mouse sera are prepared. For detection, the plates were incubated with a sheep-anti-mouse IgG-HRP detection antibody (Serotec) for 1 h at RT. 3,3',5,5'-tetramethylbenzidine (Sigma-Aldrich) was used as substrate and the reaction was stopped by adding 1 M $H_2SO_4$ (Merck). OD was measured at 450 nm with a Tecan F039300 Sunrise Absorbance Reader (Maennedorf, Switzerland).

CD8 T cell responses are measured by intracellular cytokine staining (ICCS) of CD8 T cells against interferon-γ which is produced by CD8 T cells from dVACVor mdVACV-infected C57BL/6 mice in response to contact with cells infected with the respective dVACV or mdVACV presenting CD8 T cell antigenic epitopes. Animals are immunized with $10^7$ $TCID_{50}$ or $10^8$ $TCID_{50}$ of dVACV and mdVACV by the route of choice (intramuscular, subcutaneous, intraperitoneal or intravenous) once, twice, three times or four times in 4-week intervals. In addition mice can be immunized again at least 12 weeks after the last immunization to determine CD8 T cell memory responses. Animals are bled 6 days after each immunization from the tail vein and 100-120 μl of blood per mouse are resuspended in PBS (pH 7.4) containing 4% fetal calf serum (FCS), 2 mM EDTA and 2.5 U/ml heparin. Peripheral blood mononuclear cells (PBMCs) are prepared by lysing erythroctyes using Red Blood Cell Lysing Buffer (Sigma-Aldrich, Steinheim, Germany) according to manufacturer's instructions. PBMCs are split into two aliquots at a ratio of 1:2 and the smaller aliquot of PBMCs is infected with the respective dVACV or mdVACV in RPMI/10% FCS containing 0.05 mM β-mercaptoethanol at a multiplicity of infection of 10 to obtain stimulator cells. Cells are washed in RPMI/10% FCS containing 0.05 mM β-mercaptoethanol after 1 h of incubation at 37° C. with the virus and finally resuspended in RPMI/10% FCS containing 0.05 mM β-mercaptoethanol. The remaining two thirds of the PBMCs are added to the washed stimulator cells in RPMI/10% FCS containing 0.05 mM β-mercaptoethanol and 1 μl/ml (final concentration) of GolgiPlug™ (BD Biosciences, for blocking secretion of cytokines via the exocytotic pathway), and incubated for another 5 h at 37° C. in 5% $CO_2$. Stimulated PBMCs harvested by centrifugation, resuspended in icecold PBS/10% FCS/2 mM EDTA pH 7.4 and stored overnight at 4° C. The following day, PBMCs are stained with antibodies anti-CD8α-Pac-Blue and anti-CD19-PerCP-Cy5.5 (all antibodies from BD Biosciences, Heidelberg, Germany). PBMCs are incubated with appropriate dilutions of the indicated antibodies for 30 min at 4° C. in the dark. After washing, cells were fixed and permeabilized by using the Cytofix/Cytoperm™ Plus kit (BD Biosciences) according to the manufacturer's instructions. After washing, PBMCs were stained for intracellular interferon-γ (IFN-γ) using a FITC-conjugated anti-IFN-γ antibody (BD Biosciences). The antibodies are diluted in perm/wash buffer (BD Biosciences) and the PBMCs are stained for 20 min at 4° C. in the dark. After washing, stained cells are analysed by flow cytometry on a BD Biosciences LSR II system. Live PBMCs are identified by forward and side scatter characteristics. Approximately 20,000 PBMCs are acquired per sample.

The viruses of the invention are characterized in this experiment in that the CTL immune response against the epitopes mentioned above, which is induced by the mdVACV prime/mdVACV boost administration, is substantially the same, preferably at least the same, as that induced by dVACV/dVACV boost administration, as assessed by the proportion of IFN-γ producing CD8 T cells among all CD8 T cells in PBMCs. As measures for immunogenicity, amounts of dVACV and mdVACV-specific IgG antibodies and cytotoxic CD8 T cells (CTLs) can be determined. dVACV/mdVACVspecific antibodies can be determined by standard ELISA technique using infected CEF cell lysates or purified dVACV/mdVACV as antigen and an anti-IgG-specific enzyme-coupled antibody as secondary reagent. mVACV/mdVACV-specific CTL can be determined by restimulating peripheral blood mononuclear cells (PBMC) or splenocytes with either dVACV/mdVACV as whole viruses or with specific peptides corresponding to the immunodominant epitopes derived from proteins B8, A3, K3, A8, B2 and A23 when immunizing C57BL/6 mice or from A52, F2, C6 and E3 when immunizing BALB/c mice In a preferred embodiment, instead of using $10^7$ $TCID_{50}$ mdVACV administered as in the above-assay $1\times10^8$ $TCID_{50}$ vaccinia virus of the present invention is administered by subcutaneous, intramuscular, intraperitoneal, or intravenous injection for both prime and boost immunization. The virus of the present invention is characterized in this experiment in that the CTL immune response against the epitopes mentioned above, which is induced by the mdVACV prime/mdVACV boost administration, is substantially the same, preferably at least the same, as that induced by dVACV prime/dVACV boost administration, as assessed by the proportion of IFN-γ producing CD8 T cells among all CD8 T cells in PBMCs. Alternatively, proportions of IFN-γ producing cells can be assessed by intracellular cytokine staining for IFN-γ or by staining with receptor-specific MHC class I tetramer/pentamer/dextramer reagents.

A further aspect of the invention provides a method of preparing a vaccinia virus deletion variant (dVACV), said method comprising:

a) providing a vector comprising the genome of a Vaccinia virus (VACV) or providing a genome of a Vaccinia virus (VACV);
b) deleting at least one sequence corresponding to del I, del II, del III, del IV, del V and/or del VI as set out above;
c) isolating the dVACV.

Preferably, the VACV genome replicates in a human cell line.

In a preferred embodiment, said method of preparing a dVACV comprises the step of measuring the amplification ratio of said dVACV in a human cell line (so-called first replication). Preferably, the dVACV genome which is to be prepared by the above method replicates in a human cell line. Said human cell line is preferably selected from the group consisting of MRC-5, 293 and 143B.

In some preferred embodiments of said method of preparing a dVACV the VACV is chorioallantois vaccinia virus Ankara (CVA), preferably CVA-PP as deposited under GenBank accession number AM501482 and deposited under ECACC accession number 10062901.

The product of the above method is a dVACV as set out above. Preferably, the product is a deleted CVA (dCVA) obtainable by the above method, said dCVA preferably replicates in a human cell line selected from 293, 143B and MRC-5 cell lines.

In some preferred embodiments of the dCVA obtainable by the above method, the genomes of the following viruses are excluded: vP668, vP681, vP749, vP774, vP796, vP811, MVA-I721 (GenBank accession number DQ983236) (1) and VACV strain Tian Tan mutant $MVTT_{2-GFP}$(39, 40). Also excluded is vP 759 (25). vP668, vP681, vP749, vP759, vP774, vP796 and vP811 are disclosed in Perkus et al. (25). MVA-I721 is disclosed in U.S. Pat. No. 5,185,146 (1).

In order to prepare an mdVACV as set out above, a further embodiment of this aspect of the invention provides for a method as set out above, comprising the additional step of introducing at least one mutation into the dVACV genome and isolating the resulting mdVACV.

In particular, the present invention provides a method of preparing a replication restricted mutated Vaccinia virus deletion mutant (mdVACV) comprising:

(a) providing a dVACV, preferably a dCVA as described herein;
(b) introducing at least one mutation into the genome of said dVACV, preferably dCVA; and
(c) isolating the mdVACV, preferably mdCVA.

In a preferred embodiment, said method of preparing a replication restricted mutated Vaccinia virus deletion mutant (mdVACV) further comprises the step of measuring the amplification ratio of said dVACV, preferably said dCVA in a human cell line; and/or measuring the amplification ratio of said mdVACV, preferably said mdCVA in said human cell line.

In another preferred embodiment, said method of preparing a replication restricted mutated Vaccinia virus deletion mutant (mdVACV) further comprises the step of comparing the amplification ratio of said dCVA with the amplification ratio of said mdVACV in order to determine whether the at least one mutation affects the replication of said mdVACV in said human cell line.

In a preferred embodiment said mdVACV, preferably said mdCVA is replication restricted, preferably replication incompetent in a human cell line relative to the replication of dVACV in said human cell line.

Preferably, said human cell line is selected from the group consisting of MRC-5, 293 and 143B.

The product of the method of preparing a mdVACV is preferably a chorioallantois Vaccinia virus Ankara deletion variant (mdCVA) which is obtainable by said method. Preferably, said mdCVA is replication restricted in a human cell line selected from 293, 143B and MRC-5.

In a preferred embodiment of the mdCVA, the following viruses are disclaimed: MVA-572 (ECACC V94012707), MVA-BN® (GenBank accession number DQ983238), MVA II/85, MVA (ATCC VR-1508), and NYVAC. Also excluded is Acambis 3000 modified Virus Ankara, the sequence of which is deposited with GenBank under accession number AY603355 and MVA-I721 (1).

FIGURE LEGENDS

FIG. 1. Schematic Representation of the BAC Construct and BAC-Derived MVA and CVA Viruses.

A) The construct used for homologous recombination into IGR I3L-I4L of CVA and MVA-BN® was excised from plasmid pBN194 by SacI digestion. The construct contains the genes required for BAC replication in *E. coli* as well as selection markers and was used to generate CVA-BAC1 and MVA-BN-BAC4 by homologous recombination. MVA-BN-BAC24 was created by site-directed mutagenesis of MVA-BN-BAC4 to contain two loxP sites flanking the BAC backbone. Reconstitution of the BACs yielded $CVA_B$ and $MVA_B$, respectively. F1 IGR I3L-I4L and F2 IGR I3L-I4L=left and right flanks for homologous recombination into the CVA and MVA-BN® genomes. NPT II, IRES, EGFP are combined to a marker cassette driven by the pS promoter. RFP driven by the pS promoter and flanked by two FRT sites was used as a transient marker for monitoring Flp recombinase activity. CmR=chloramphenicol acetyltransferase resistance marker for selection in *E. coli*. B) Schematic representation of the mutagenesis process used to generate a mutant CVA containing all major MVA-like deletions. Relative positions of the genomic segments corresponding to the six major MVA deletions are indicated by boxes designated del I, del II, etc. Sequential removal of these regions to delete these sequences from CVA and the designation of the mutants is indicated from top to bottom. ORFs that have been introduced to exactly mimic the MVA sequence at these sites are indicated at the respective deletion sites. The selection cassette used to introduce deletion I has been removed by Cre-lox recombination leaving a single loxP site ("loxP"). VARV=variola virus, CPXV=cowpox virus, (f)=fragmented ORF.

FIG. 2. Replication Properties and Pathogenicity of BAC-Derived Viruses $MVA_B$ and $CVA_B$ are Indistinguishable from Those of the Corresponding Parental Wild-Type Viruses.

Replication behavior of $MVA_B$ (A) and $CVA_B$ (B) was analyzed in various cell lines and primary CEF cells and was compared to that of the corresponding wild-type viruses MVA-BN© and CVA-PP. Cells were infected in triplicate with 0.05 $TCID_{50}$/cell of the indicated viruses. Total viral output at the indicated times is plotted, each data point represents results from three independent wells. The value of $5\times10^4$ $TCID_{50}$ at day 0 represents the inoculum titer. Survival (C, D), body weight loss (E) and disease symptoms (F) after infection of 6-8 week old BALB/c mice were determined. Animals were infected intranasally with $10^7$ (C, D, F; open symbols) and $5-7\times10^7$ $TCID_{50}$ (D, E, F; filled symbols) of parental virus CVA-PP (squares) and $CVA_B$ (triangles). The experiment was performed with the indicated number (n) of mice in 2-3 independent experiments. Animals from one representative experiment were individually weighed and inspected at the indicated days (E, F). In this particular experiment, all animals infected with $10^7$ $TCID_{50}$ of CVA-PP died, whereas two out of 5 animals infected with $CVA_B$ survived. Body weight data are expressed as percentage of mean weights of the respective group compared to the initial mean group weight at day 0. Disease scores were individually determined at the indicated days according to the above-described scoring system ranging from scores 0-4. Disease scores are depicted as the mean+SEM of groups of five mice of a representative experiment.

*Body weights and disease scores of the group receiving $10^7$ $TCID_{50}$, of $CVA_B$ after day 11 p.i. is based on the values of the two surviving animals.

FIG. 3. MVA-Like Cytopathic Effect of Del II-Containing Mutants and In Vitro Replication Analysis of Mutants mCVAbc45 and mCVAbc50.

A) Primary CEF cells were infected with 0.05 $TCID_{50}$/cell of the indicated viruses. For visual characterization of CPE, the infected cell monolayers were inspected daily by fluorescence microscopy: Infected cells show green fluorescence due to eGFP expression by the recombinant viruses and were photographed at 100× magnification on day 3 p.i. Cytopathic effect of mutants mCVAbc48 and mCVAbc50 was indistinguishable from that of mutants mCVAbc39 and mCVAbc45 and is therefore not shown here. B) For analysis of multi-step replication of wild-type CVA, mCVAbc45 and mCVAbc50 in CEF cells and mammalian cell lines, monolayers of approximately $10^6$ primary CEF cells or the indicated cell lines were infected in triplicate with 0.05 $TCID_{50}$/cell of the indicated viruses. Total viral output at the indicated times is plotted, each data point represents results from three independent wells. The value at day 0 represents the inoculum titer ($5\times10^4$ $TCID_{50}$).

FIG. 4. Pathogenicity of CVA Mutants Containing Up to Six Major MVA-Like Deletions in Mice.

Groups of five 6-8 week old female BALB/c mice were intranasally infected with $3\times10^6$ $TCID_{50}$ (A-D) or $5\times10^7$ $TCID_{50}$ (E-H) of the indicated viruses in 50 μl PBS and animals were individually weighed and inspected daily. Body weight data are expressed as percentage of mean weights of the respective group from the initial mean weight at day 0. Mean disease scores+/−SEM were determined at the indicated days according to the above-described scoring system ranging from scores 0-4. The same MVA-infected control groups are shown in A and B, and in E and F, respectively.

One animal each from the groups that received mutant mCVAbc39 (E) or mCVAbc50 (F) succumbed to disease at day 7 and 10, respectively. A-D show combined data from three independent experiments. E-H show one of at least two independent experiments. I) For analysis of Viral titers in lungs of infected mice, groups of 6-8 week old female BALB/c mice were intranasally infected with $3\times10^5$ $TCID_{50}$ of the indicated viruses in 50 μl PBS. Animals were sacrificed at day six p.i., lungs were recovered and homogenized in 2 ml of cell culture medium. Viral titers were determined by the $TOID_{50}$ method on CV-1 cells (CVA viruses) or CEF cells ($MVA_B$) and average viral titers per organ from totally 8 mice from two independent experiments are shown. ***=$p<0.001$ as determined by Student's t test. n.s., not statistically significant. n.d., not detected. The detection limit of the assay is $3.16 \times 10^1$ TCID$_{50}$/ml.

Figure 5A:
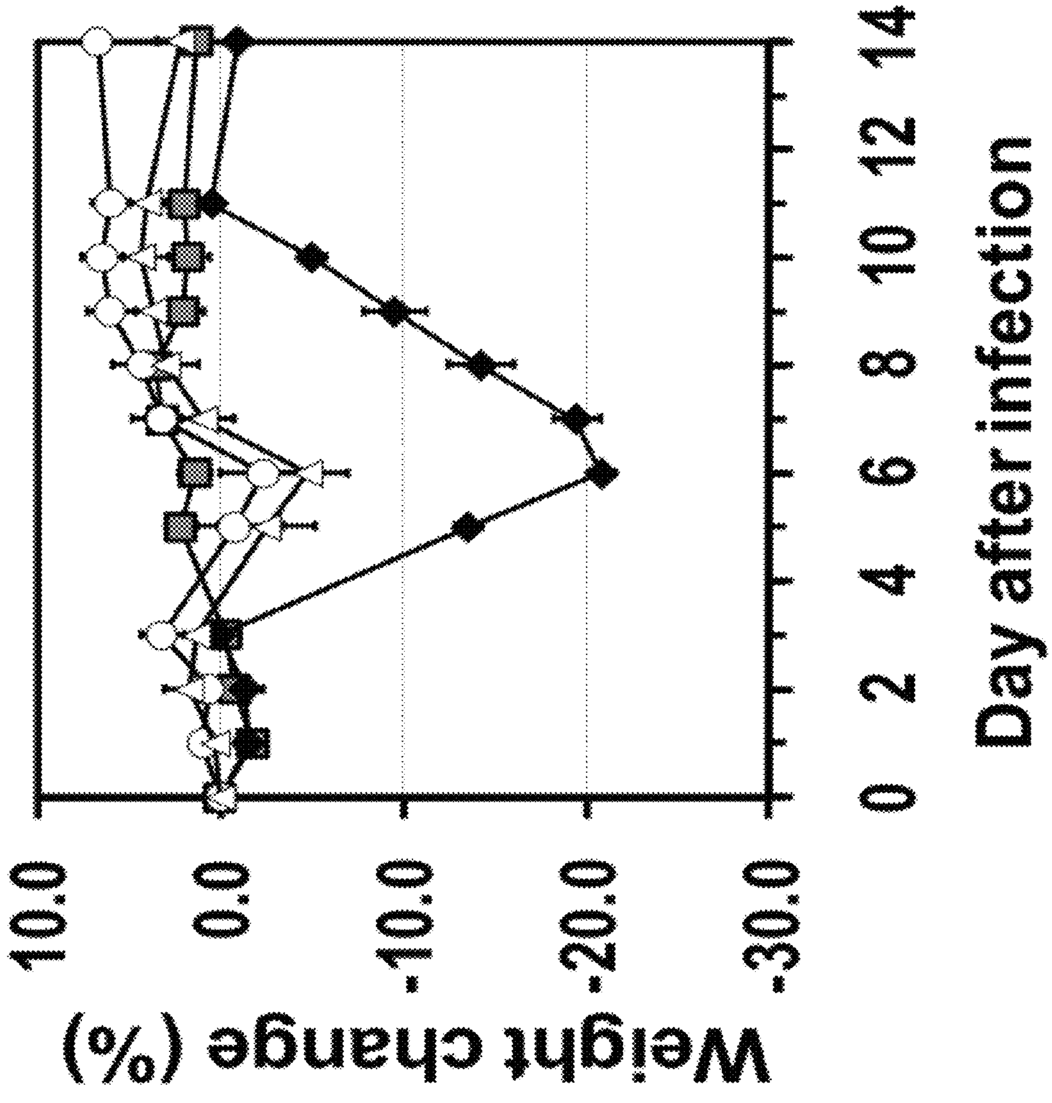
Figure 5B:
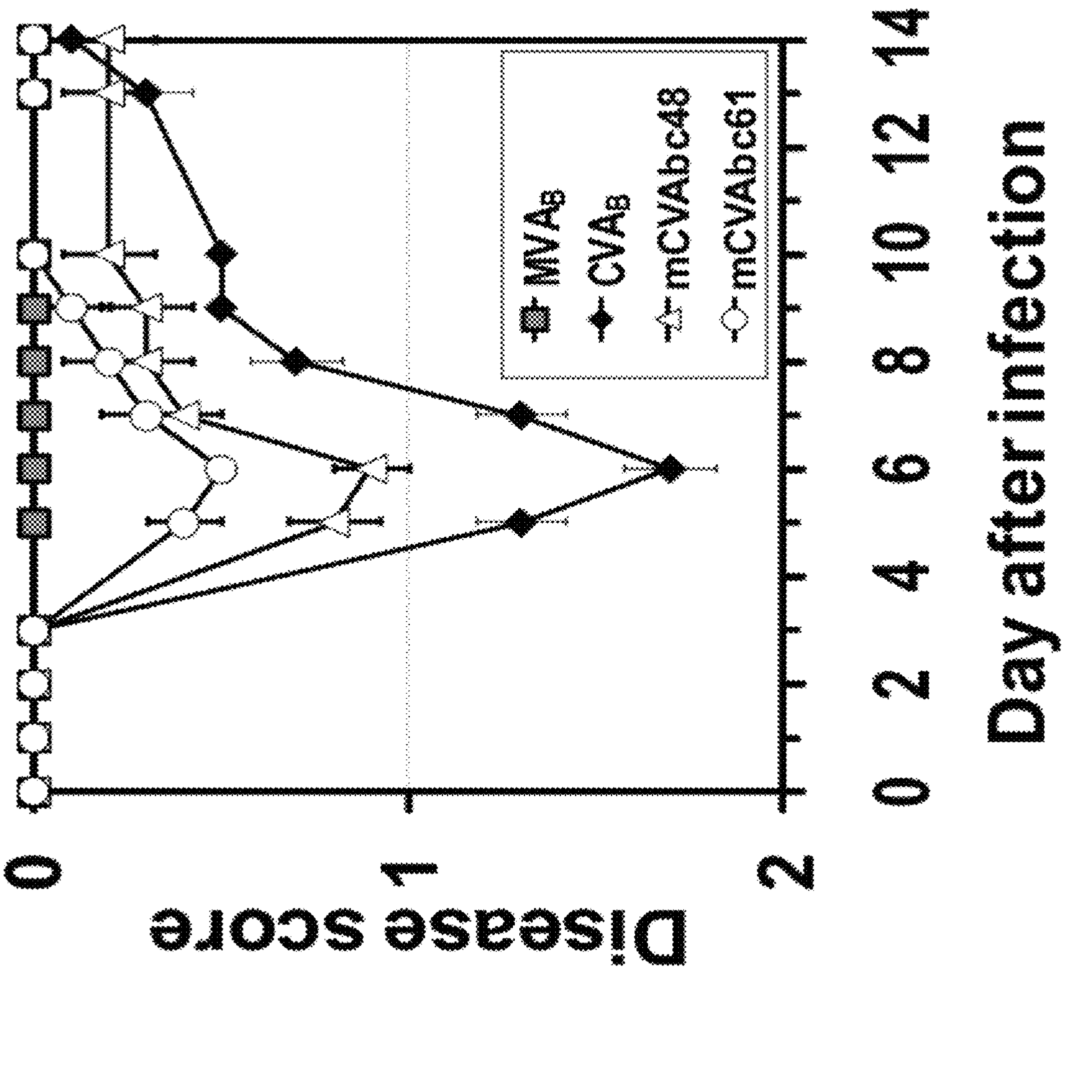

FIG. 5. A Mutant Containing Deletion V Alone is Moderately Attenuated.

Groups of five 6-8 week old female BALB/c mice were intranasally infected with $3 \times 10^5$ TCID$_{50}$ (A-C) or $1 \times 10^7$ TCID$_{50}$ (D) of the indicated viruses in 50 µl PBS and animals were individually weighed (A) and inspected (B) daily. Separate groups of five mice each infected with CVA$_B$ and mCV-Abc61 were sacrificed at day six p.i. and lungs were recovered and homogenized in 2 ml of cell culture medium to determine infectious viral titers (C, D). Body weight data are expressed as percentage of mean weights of the respective group from the initial mean weight at day 0. Mean disease scores+/−SEM were determined at the indicated days according to the above-described scoring system ranging from scores 0-4. Data from one out of two independent experiments are shown. The MVA-infected control group is the same as in FIG. 4A-D. ** $p<0.01$ as determined by Student's t test.

Figure 6:
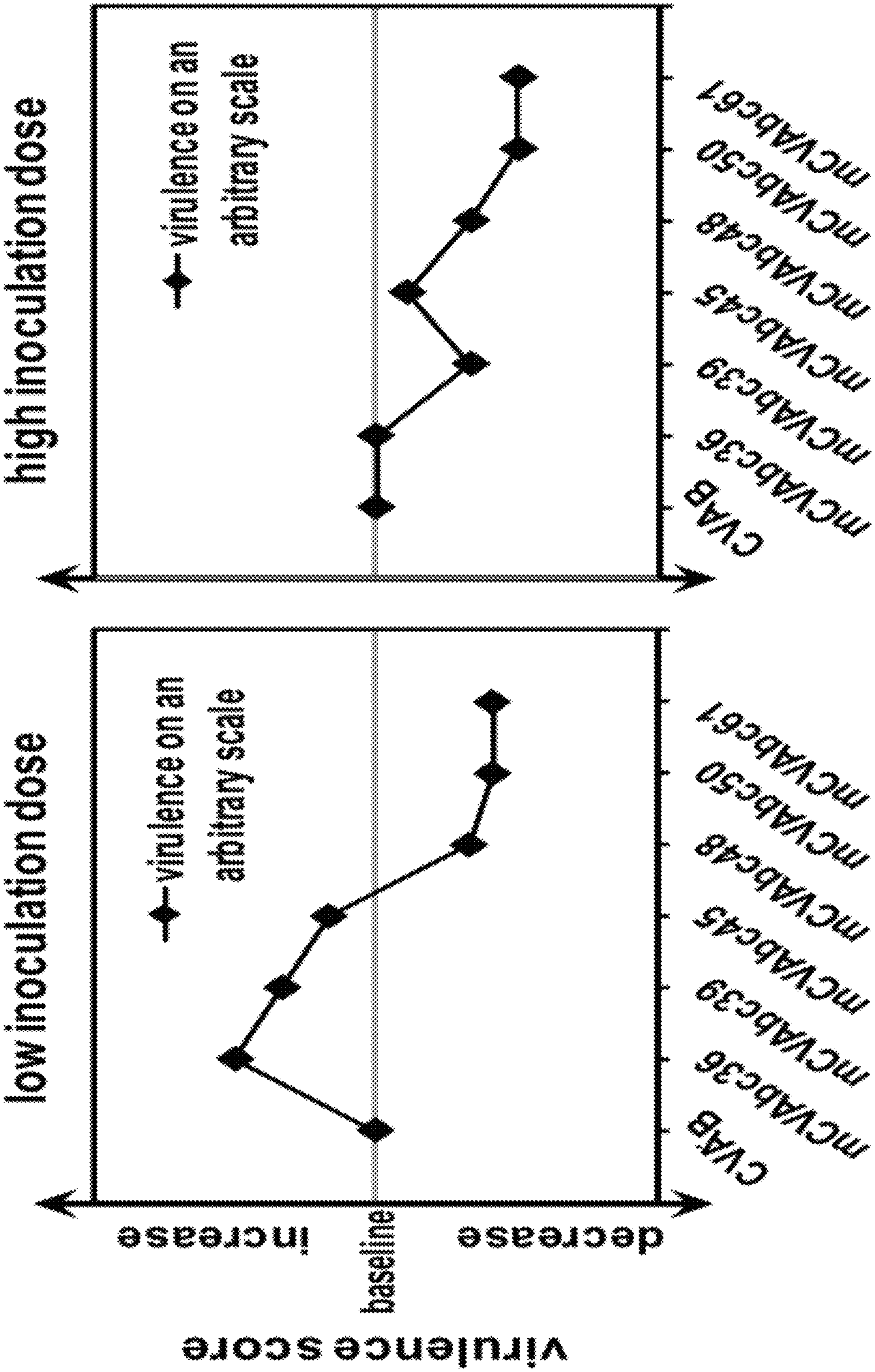

FIG. 6. Schematic Representation of the Virulence of CVA Mutants Containing MVA-Like Deletions.

The virulence score arbitrarily combines the parameters maximum weight loss; maximum disease score; kinetics of recovery. The parameters were weighted according to the above order.

TABLE 1

Full-Length Genes Contained in the Six Major MVA-Like Deletions

* Full length genes are defined as genes encoding proteins with similar amino acid numbers like their cowpoxvirus orthologues. Of the 31ORFs in the six major deletions, 19 ORFs represent fragments or truncated forms of full-length cowpox genes and are therefore not shown in the table.

TABLE 2

Virus Spread of Various CVA Mutant Viruses in Various Cell Lines $^a$: Virus spread as visualized by fluorescence 48 h post infection with 0.05 TCID$_{50}$/cell. Virus spread was scored according to the following arbitrary scale: −, No fluorescent cells; +, foci of 1 to 4 fluorescent cells; ++, foci of 5 to 25 fluorescent cells; +++, foci of >25 fluorescent cells or confluent infection, respectively.

EXAMPLE

Introduction of the Six Major Genomic Deletions of Modified Vaccinia Virus Ankara (MVA) into the Parental Chorioallantois Vaccinia Virus Ankara (CVA) is not Sufficient to Reproduce an MVA-Like Phenotype in Cell Culture and in Mice Summary Modified vaccinia virus Ankara (MVA) has a highly restricted host range in cell culture and is apathogenic in vivo. MVA was derived from the parental chorioallantois vaccinia virus Ankara (CVA) by more than 570 passages in chicken embryo fibroblasts (CEF) cells. During CEF cell passaging, six major deletions comprising 24668 nucleotides occurred in the CVA genome. We have cloned both the MVA and the parental CVA genome in bacterial artificial chromosomes (BACs) and have sequentially introduced the six major MVA deletions into the cloned CVA genome. Reconstituted mutant CVA viruses containing two to six major MVA deletions showed no detectable replication restriction in 12 mammalian cell lines tested except in rabbit cell lines RK13 and SIRC. In mice, CVA mutants with up to three deletions showed slightly enhanced virulence indicating that gene deletion in VACV can result in gain of fitness in vivo. CVA mutants containing 5 or all 6 deletions were still pathogenic, with a moderate degree of attenuation. Deletion V was mainly responsible for the attenuated phenotype of these mutants. In conclusion, combined loss or truncation of all 31 open reading frames in the six major deletions is not sufficient to reproduce the specific MVA phenotype of strong attenuation and highly restricted host range.

Material and Methods

Cell Lines and Viruses

All cell lines were obtained from ATCC or European Collection of Cell Cultures except HaCaT cells (6) which were obtained from the German Cancer Research Center (DKFZ), Heidelberg. All cell lines were grown in Dulbecco's modified Eagle medium (DMEM, Gibco) supplemented with 10% fetal calf serum (FCS, Pan Biotech, Germany). Primary CEF cells were prepared from 11 day-old embryonated chicken eggs and cultured in VP-SFM (Gibco) or Dulbecco's modified Eagle medium supplemented with 10% FCS. CVA was obtained from Anton Mayr (Veterinary Faculty, Ludwig-Maximilians University of Munich, Munich, Germany) and was plaque-purified three times on BHK-21 cells and amplified for two rounds on CEF cells resulting in CVA-PP (19). The virus strain CVA-PP has been deposited with the ECACC and has been assigned the accession number 10062901. The nucleotide sequence of the coding region of CVA-PP was determined and deposited in GenBank under accession no. AM501482. All mutants derived from CVA-PP were propagated and titered on CV-1 cells. MVA-BN® was developed by Bavarian Nordic and deposited at European Collection of Cell Cultures (ECACC; V00083008). MVA-BN® was propagated and titered on CEF cells. Shope Fibroma Virus (SFV) was obtained from ATCC (VR-364) and was propagated and titered on SIRC cells. All viruses used for sequencing and in animal experiments were purified twice through a sucrose cushion.

Plasmids

The miniF BAC plasmid pMBO131 (22) was kindly provided by M. B. O'Connor. Recombination plasmid pBN194 (FIG. 1A) was cloned by standard methods and contained the entire sequence of pMBO131 plus an NPT II-IRES-eGFP reporter/selection cassette driven by the strong synthetic early/late pS promoter (8). It further contained an RFP reporter gene driven by the pS promoter and flanked by FRT sites. These sequences are flanked by two stretches of sequences for homologous recombination derived from the left and right sides of the insertion site in the intergenic region (IGR) between I3L (ORF MVA 064L, ssDNA-binding phosphoprotein) and I4L (ORF MVA 065L, ribonucleotide reductase large subunit) of MVA-BN® and CVA. Plasmid pOG44 expressing Flp recombinase was purchased from Invitrogen. Plasmid pKD46 (10) encoding the recombination functions redo (exo), redβ (bet) and the exonuclease inhibitor redγ (gam) was kindly provided by U. Koszinowski, Ludwig-Maximilians University, Munich, Germany. Koszinowski.

Construction of preCVA-BAC and preMVA-BAC

Plasmid pBN194 was used to generate the viruses preCVA-BAC and preMVA-BAC that represent recombinant CVA-PP and MVA-BN® containing the entire sequence of the BAC vector pMBO131 plus selection markers at the IGR 3L-I4L of CVA and MVA. While the experiments here were performed using the BAC vector as described below, it is noted that other recombinant vectors would also be suitable. The skilled person knows that the teaching herein within the context of the BAC vector may be routinely applied to other recombinant vectors besides the specific BAC vector constructed and employed here. Alternatively, the mutations can be introduced into a VACV without using cloned VACV genomes in BACs by employing transient-dominant selection (13).

To construct BACs containing the CVA and MVA genomes, respectively, the pBN194 plasmid was linearized with Sac I and transfected into CVA- and MVA-infected monolayers of nearly confluent CEF cells using Fugene HD (Roche Diagnostics, Mannheim, Germany). At 48 h after infection, cells and medium were harvested, freeze-thawed and homogenized in a cup sonicator. Selection for recombinant virus was performed on CEF cells in 6-well plates using G418 (Geneticin®, Invitrogen, Karlsruhe, Germany) at a concentration of 300 μg/ml. Plaque purifications of single viral clones were performed on CEF cells in 96-well plates using 10-fold serial dilutions and screening for wells containing single virus plaques visualized by eGFP expression. Viral DNA from several clones was analyzed by PCR and sequencing to confirm correct mutagenesis.

Generation of CVA-BAC and MVA-BAC

Cloning of the MVA and CVA genomes as BACs was basically done as previously described with minor modifications (11). CEF cells in 6-well plates were transfected with 2 μg of Flp-expressing plasmid pOG44 using Fugene HD (Roche Diagnostics). After 60 min at 37° C. the cells were infected with preCVA-BAC or preMVA-BAC at a multiplicity of infection (m. o. i.) of 5 and isatin-β-thiosemicarbazone (IβT) was added to a final concentration of 45 μM. At 24 h after infection, the cells were harvested and DNA was phenol-extracted and precipitated as described (11) and dissolved in 20 μl $ddH_2O$. Eight μl of isolated viral DNA was used for electroporation into DH10B *E. coli* (Invitrogen). Selection of *E. coli* containing viral DNA as BAC plasmid was performed on LB plates containing Chloramphenicol at a concentration of 25 μg/ml. DNA from multiple clones was isolated by alkaline lysis from liquid LB cultures and screened by digestion with suitable restriction enzymes (NEB, Frankfurt, Germany, and Roche Diagnostics). BAC-DNA of candidate clones containing the complete viral DNA, was prepared using the Macherey-Nagel NucleoBond BAC 100 Kit (Macherey-Nagel, Düren, Germany) and extensively screened by digestion with several restriction enzymes and overnight electrophoresis. The BAC-DNA of one clone each of CVA-BAC and MVA-BAC was directly sequenced to confirm sequence integrity.

Reactivation of Infectious Virus

BHK-21 cells in a 6-well plate were transfected with 3 μg of BAC DNA using Fugene HD and 60 min later infected with SFV to provide the helper functions. The cells were monitored for eGFP expression and development of cytopathic effect (CPE) and harvested three days later. After freeze-thawing and homogenization in a cup sonicator, graded amounts of the lysate was used to infect CEF cell monolayers. The cells were monitored for the appearance of virus growth. After three passages in CEF cells to remove the helper SFV, total DNA was extracted from infected cells of the last passage and screened by PCR for absence of SFV. The rescued BAC-derived viruses were designated $CVA_B$ and $MVA_B$, respectively, and were propagated in CV-1 ($CVA_B$) and CEF cells ($MVA_B$).

BAC Recombineering

CVA-BAC was modified by allelic exchange in DH10B *E. coli* utilizing the λ Red system for homologous recombination. (a) Introduction of pKD46 into *E. coli*. Electrocompetent *E. coli* DH10B cells containing the CVA-BAC were electroporated pKD46 plasmid and plated on LB plates containing 25 μg/ml of chloramphenicol and 50 μg/ml of ampicillin and incubated overnight at 30° C. (b) Induction of the λ Red system. DH10B cells containing the BAC of interest and pKD46 encoding the three proteins γ, β, and exo constituting the Red recombinase (10) were propagated at 30° C. to an $OD_{600}$ of 0.3. The λ Red genes were induced by addition of L-arabinose (Merck, Darmstadt, Germany) to a final concentration of 0.4% and incubation at 37° C. for 60 min prior to electroporation. (c) Introduction of the selection/counterselection cassette. Deletions were obtained by introducing a cassette containing the neomycin resistance gene for positive selection and the rpsL gene for counterselection (26,35,38). Briefly, oligonucleotides of 74 bp length (Metabion, Martinsried, Germany) containing the regions of homology to CVA (50 bp) and sequences complementary to the ends of the rpsL-neo cassette (24 bp) were used to add homology arms to the 5' and 3' ends of the selection-counterselection cassette by PCR. The PCR products were then electroporated into L-arabinose-induced *E. coli* carrying CVA-BAC and pKD46. Selection was performed on LB plates containing 25 μg/ml of chloramphenicol, 25 μg/ml of kanamycin and 50 μg/ml of ampicillin at 30° C. overnight. (d) Replacement of rpsL-neo by non-selectable DNA. The cassette was replaced by electroporation of non-selectable DNA into rpsL-neo-BAC- and pKD46-containing DH10B and induction of homologous recombination as described above. The non-selectable DNA was generated by PCR with long oligonucleotide primers adding 50 bp homology arms at both ends of the non-selectable DNA. To tracelessly remove the rpsL-neo cassette without any further insertion of DNA, a single-stranded oligonucleotide consisting of 30 bp homology arms at both sides of the insertion site of the rpsL-neo cassette was used. Streptomycin (75 μg/ml) was used for counterselection to obtain rpsL-neo-negative BAC clones. The modified BACs were analyzed by digestion with several restriction enzymes and by direct sequencing of the region containing the introduced modifications. The removal of the selection cassette was further confirmed by nested PCR. Absence of insertion sequence (IS) elements was confirmed by PCR for *E. coli* IS elements 1, 2, 3, 4, 5, 10, 30, 150, and 186.

Sequencing

BAC DNA was amplified in DH10B *E. coli* and isolated using the Macherey-Nagel NucleoBond BAC 100 kit. For sequencing of mCVAbc39 and mCVAbc50, genomic DNA of MVA and CVA was isolated from $2\times10^7$-$1\times10^8$ $TCID_{50}$ of purified viral stock suspensions with a commercially available kit (NucleoSpin™ Blood Quick Pure, Macherey-Nagel, Düren, Germany). Purified viral genomic DNA or BAC DNA was used as template to amplify DNA fragments of ~5 kB covering the complete coding sequence starting between the repetitive sequences of the left inverted terminal repeat (ITR) and open reading frame (ORF) MVA001L and CVA001, respectively, and extending through ORF MVA193R and CVA229, respectively with an overlap of ~500 bp each. Briefly, PCR fragments were amplified using the TripleMaster™ PCR system (QIAGEN, Hilden, Germany) and purified with the QIAquick PCR purification kit (QIAGEN, Hilden, Germany). The PCR fragments and the purified BAC-DNA were directly sequenced by Sequiserve GmbH (Vaterstetten, Germany) with an Applied Biosystems 3730 DNA Analyzer and Sequencing Analysis software v5.0 using 10-14 customdesigned primers per PCR fragment. Contigs were assembled and analyzed using Vector NTI Advance® 9.1.

Viral Replication Analysis

For analysis of virus replication and spread, confluent monolayers in 6-well culture plates were infected at 0.05 $TCID_{50}$ per cell using $5\times10^4$ $TCID_{50}$ in 500 μl of DMEM without FCS. After 60 min at 37° C., cells were washed once with DMEM and further incubated with 2 ml of DMEM containing 2% FCS. Cells and supernatant were harvested at the indicated time points, freeze-thawed, sonicated and titrated on CEF cells according to the $TCID_{50}$ method as described (28). Briefly, serial dilutions of virus suspensions were plated on CEF cell monolayers grown in 96-well plates as replicates of 8. Cells were fixed with methanol:acetone 50/50 (v/v) five days p.i., and foci of infected cells were visualized by immunostaining. Fixed and permeabilized monolayers were incubated for 30 min with rabbit polyclonal vaccinia virus antibody (Quartett Immunodiagnostika, Berlin, Germany) diluted 1:1000 with PBS/3% FCS followed by incubation with horseradish peroxidase-conjugated polyclonal goat anti-rabbit IgG antibody (Promega, Mannheim, Germany) diluted 1:1000 in PBS/3% FCS for 30 min. After washing, cells were incubated with TMB:PBS substrate solution (Seramun Diagnostica, Heidesee, Germany) for 15 min. Infected wells were identified by purple staining of cells and the infectious titer was calculated using the $TCID_{50}$ method of Spearman and Kärber (14,27).

Mouse Infection Experiments

Female BALB/c mice aged 6-8 weeks were purchased from Harlan Winkelmann, Germany. Mice were anaesthetized by ketamine/xylazine injection prior to intranasal infection with $3\times10^5$ or $5\times10^7$ $TCID_{50}$ of MVA, CVA and CVA mutants diluted in PBS to a final volume of 50 μl per mouse. Animals were weighed and inspected daily and the signs of illness were scored on an arbitrary scale from 0-4. Score 0=healthy; score 1=slightly sick, with moderately hunched back and ruffled fur, normal mobility and activity level; score 2=sick, with clearly hunched back and ruffled fur, reduced mobility and activity level, moderate respiratory distress; score 3=very sick, with strongly hunched posture and ruffled fur, strongly reduced mobility and activity, hedgehog-like gait with coordination problems, significant respiratory distress; score 4=moribund. All animal experiments were approved by the Government of Upper Bavaria (Regierung von Oberbayern) and were carried out in accordance with the guidelines for animal experiments of Bavarian Nordic GmbH.

Results

Cloning of the CVA and MVA Genomes as BACs and Reactivation of Infectious Virus.

Figure 1A:
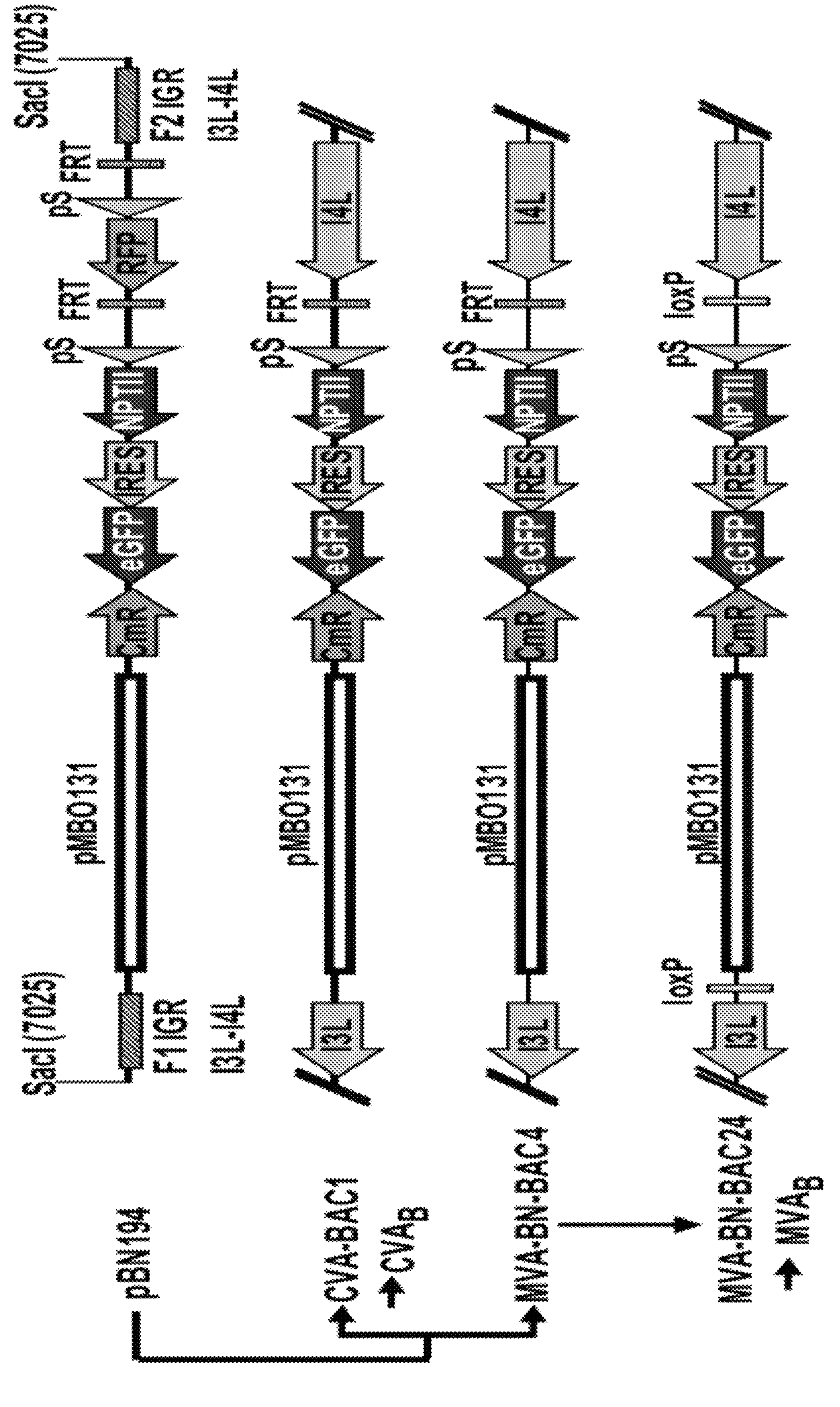

A procedure similar to that developed by Domi and Moss for VAC-BAC (11) was used to generate BACs containing the genomes of CVA and MVA-BN®. A BAC cassette was constructed containing miniF plasmid sequences for maintenance in *E. coli*, a NPT II-IRES-eGFP marker cassette driven by the poxyiral synthetic promoter (pS) and a red fluorescent protein (RFP) driven by pS and flanked by FRT recombination sites (FIG. 1A). This BAC cassette was inserted into the intergenic region (IGR) between ORFS I3L and I4L of CVA and MVA by homologous recombination (FIG. 1A), resulting in viruses preCVA-BAC and preMVA-BAC. The NPT II-IRES-eGFP cassette allowed selection of recombinant CVA and MVA viruses containing the BAC cassette. CEF cells were transfected with a Flp-expressing plasmid, infected with the recombinant viruses and simultaneously treated with isatin-β-thiosemicarbazone (IβT) to inhibit viral hairpin resolution and promote genome concatemerisation as previously described (11). Flp recombinase was expressed in infected cells to enhance circularization of unit-length genomes (11). The RFP gene flanked by FRT sites served as a marker to monitor Flp recombinase activity. DNA from transfected and infected cells was extracted and used to transform *E. coli*. Several clones yielding a correct restriction endonuclease pattern were amplified and further characterized by DNA mapping with various restriction enzymes. Interestingly, the RFP gene was found to be deleted in the preCVA-BAC virus before any induction of Flp expression while one FRT site remained. Possibly, the recombinogenic potential of vaccinia virus was able to delete the RFP gene by homologous recombination via the FRT sites. On the other hand, some BAC clones still contained the RFP gene flanked by FRT sites suggesting that circularization of unit length genomes occurred independent of Flp recombinase activity confirming previous observations (11). The BAC backbone of the initial MVA-BN-BAC4 was further modified by flanking with loxP sites (FIG. 1A) to allow excision of the BAC sequences by overexpression of Cre recombinase. For both CVA and MVA, one BAC clone with the correct restriction pattern was selected and the sequence of the coding region was determined by direct sequencing of BAC DNA. The sequences of the coding regions of both the CVA and the MVA BAC clones exactly matched the published sequences of CVA (GenBank AM501482) and MVA-BN®.

Reactivation of infectious $CVA_B$ and $MVA_B$ from the respective BAC clones ("rescue") was accomplished using SFV as helper virus (37) to provide the poxyiral transcription system required to generate authentic viral genomes from the transfected BAC that are packaged into infectious progeny virus. After BAC transfection and SFV infection of BHK-21 cells, infectious $CVA_B$ and $MVA_B$ could be rescued. To remove the helper virus, three passages on CEF cells were performed which are non-permissive for SFV. A sensitive PCR assay confirmed that no SFV DNA and thus no infectious SFV was present in stocks of rescued virus after three CEF cell passages (data not shown).

Analysis of BAC-Derived $MVA_B$ and $CVA_B$

Figure 2A:
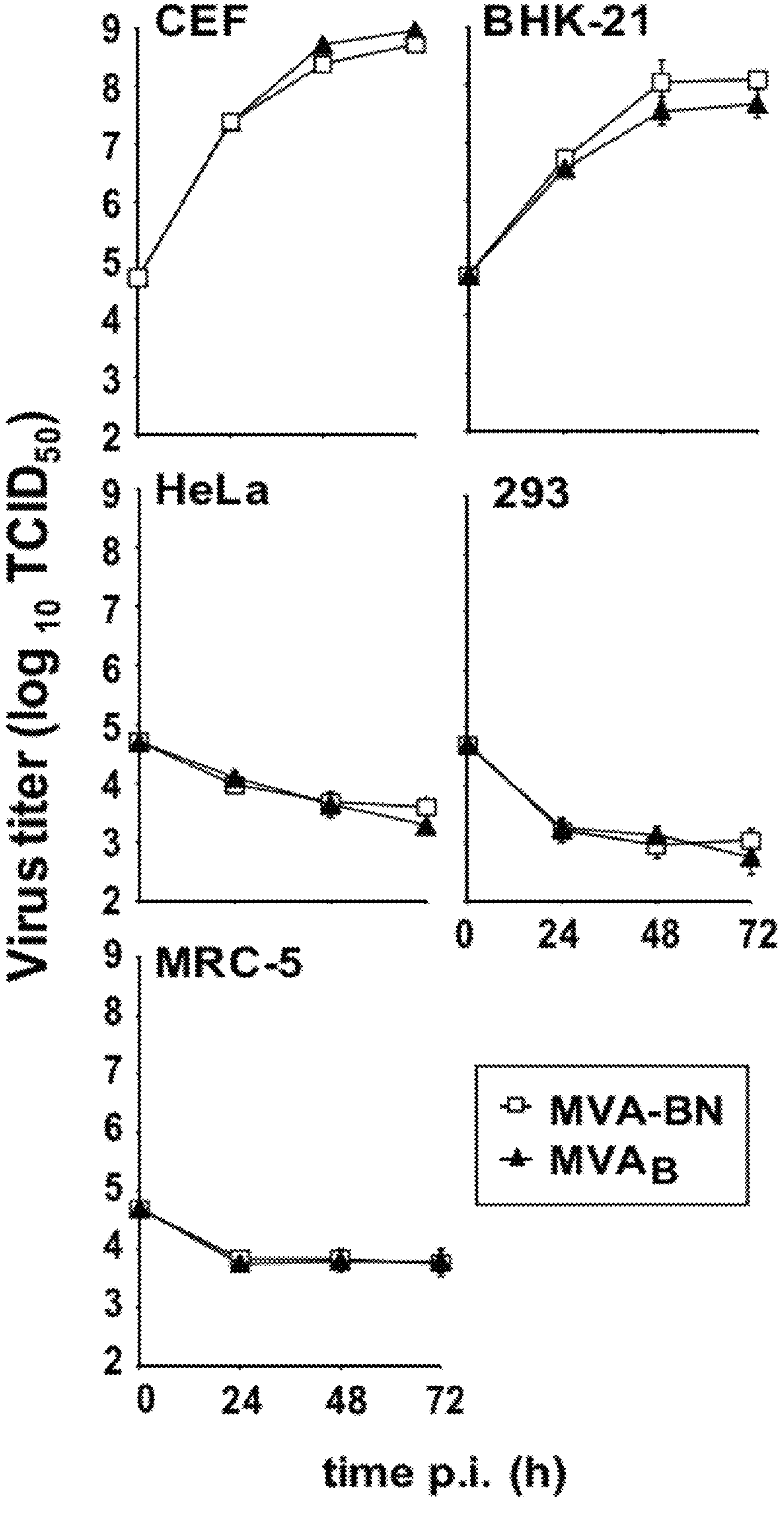

Replication characteristics of BAC-derived $MVA_B$ were compared to that of the parental MVA-BN® in both permissive and non-permissive cell systems. Replication capacity of $MVA_B$ in permissive primary CEFs and in the permissive hamster cell line BHK-21 was equivalent to that of MVA-BN® (FIG. 2A). Similarly, $MVA_B$ was unable to replicate in the non-permissive human cell lines 293, MRC-5 and HeLa like MVA-BN®.

Figure 2B:
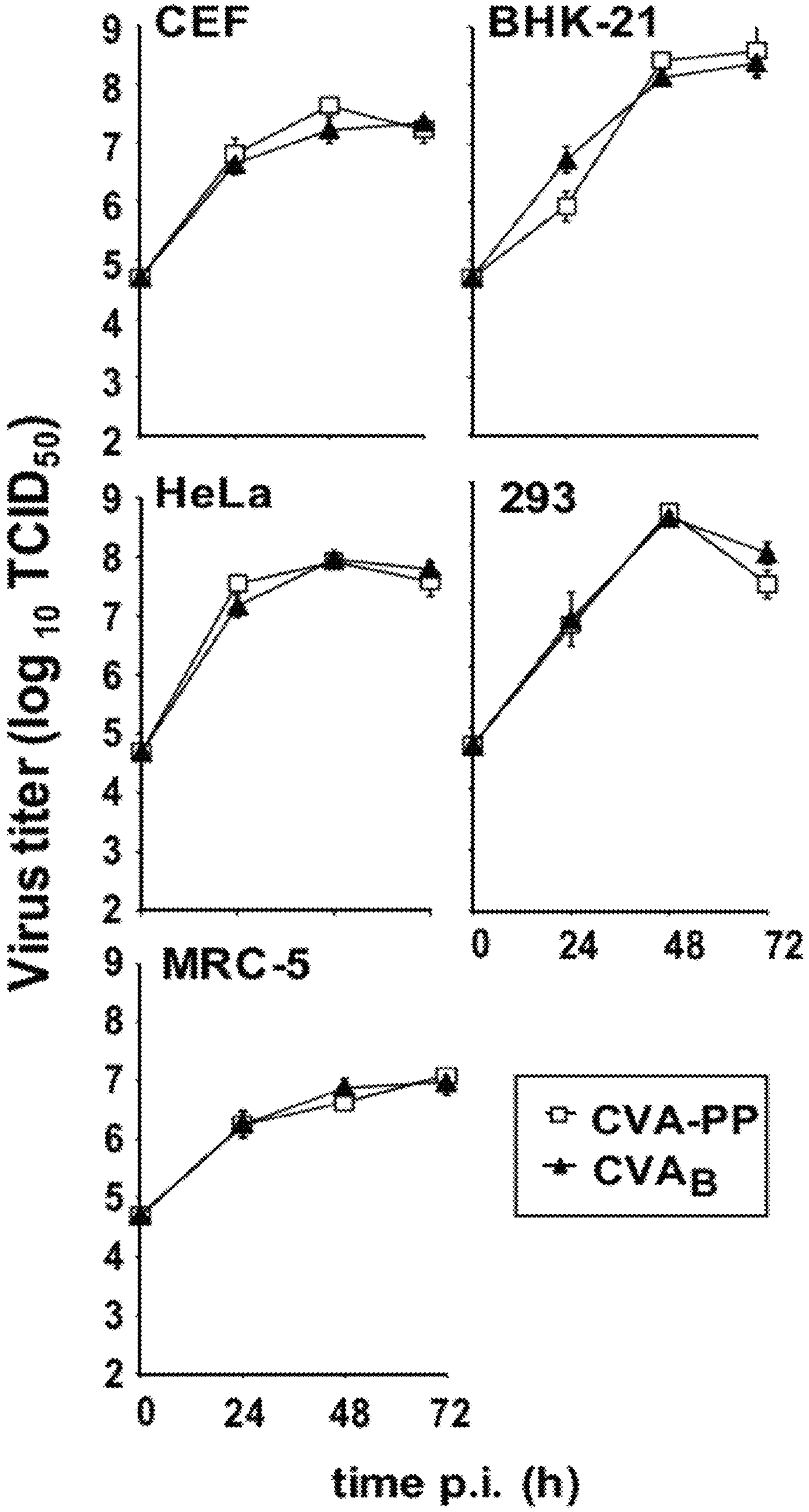

Replication characteristics of BAC-derived $CVA_B$ were also compared to its parental virus CVA-PP in various cell lines. Viral yields of $CVA_B$ from primary CEF cells as well as from cell lines of human (293, HeLa, MRC-5), and hamster origin (BHK-21) were equivalent to those obtained with the parental CVA-PP (FIG. 2B). Taken together, replication characteristics of $CVA_B$ and $MVA_B$ in permissive and non-permissive cell cultures were indistinguishable from those of their respective parental viruses CVA-PP and MVA-BN®.

Figures 2C, 2D:
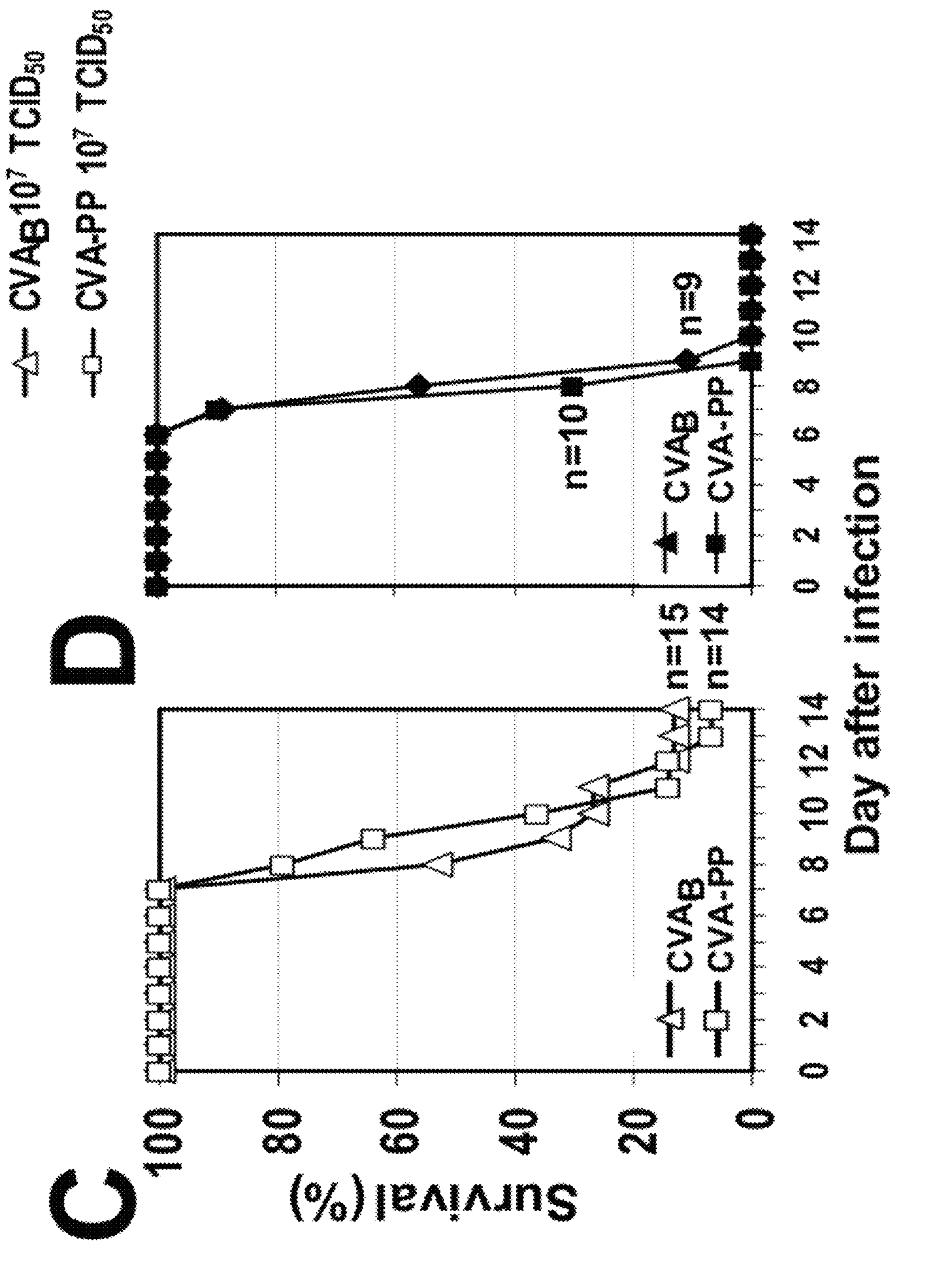
Figures 2E, 2F:
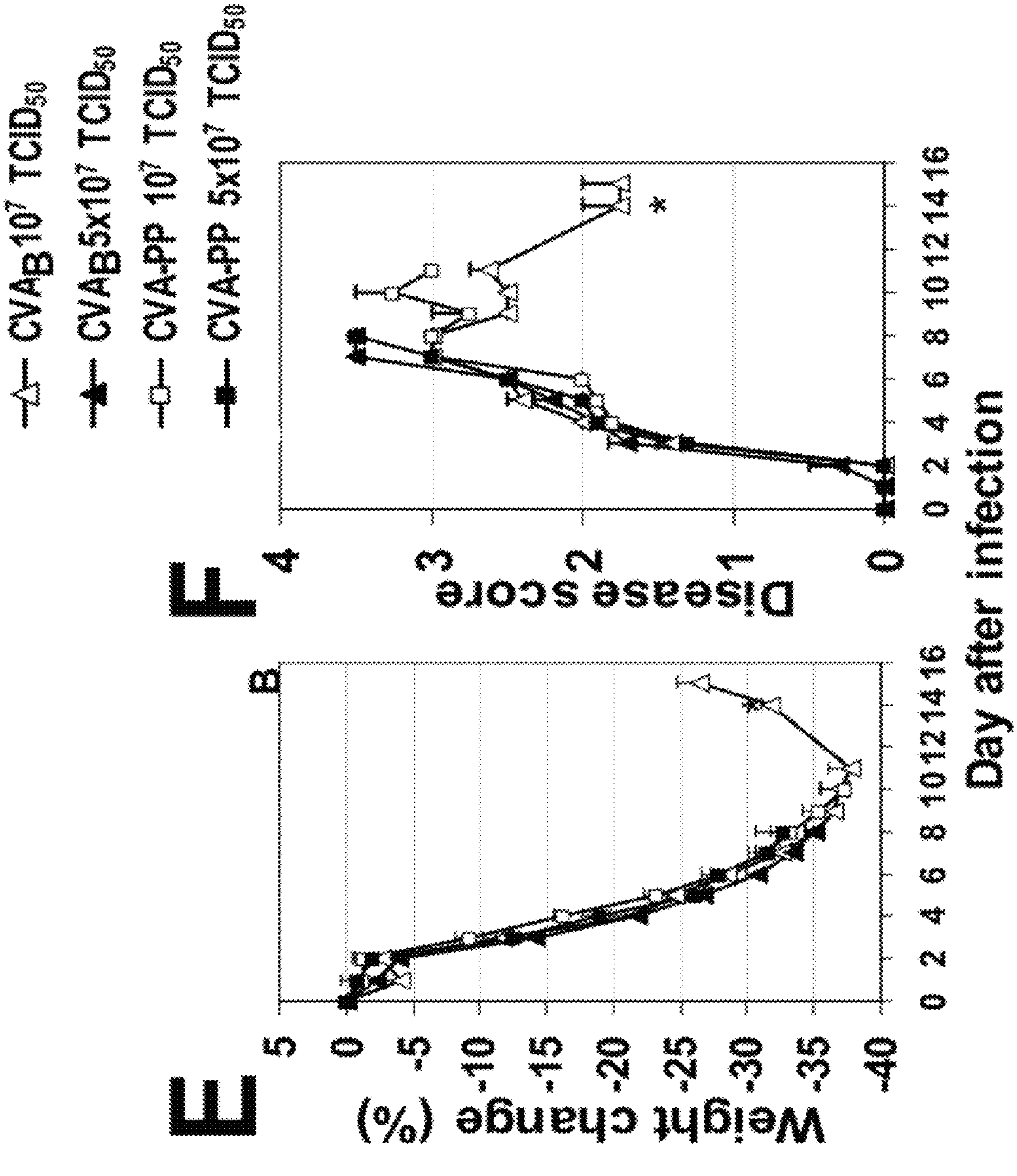

The virulence of BAC-derived $CVA_B$ was further characterized in comparison to its parent CVA-PP in 6 to 8 week old BALB/c mice by assessing weight loss and survival after intranasal infection. Since CVA is less pathogenic for mice than the mouse-adapted VACV-WR upon intranasal infection, we used inoculation doses of $10^7$ and $5\text{-}7\times10^7$ $TCID_{50}$ per mouse. The death rate was between 80 and 90% at a dose of $10^7$ and increased to 100% at a dose of $5\text{-}7\times10^7$ for both viruses (FIG. 2C, D). At both doses, weight loss and disease symptoms were very similar for both CVA-PP and $CVA_B$ (FIG. 2E, F). Severe weight loss and disease started at day 3 p.i. with both wild-type viruses (FIG. 2E, F) and the last animals died at day 9 p.i. with a mean time to death of 8.4 and 8.6 for $CVA_B$ and CVA-PP, respectively. In conclusion, $CVA_B$ and $MVA_B$ showed no detectable differences in replication and pathogenicity compared to the parental plaque-purified CVA-PP and MVA-BN® viruses.

Deletion of CVA Genes by BAC Recombineering and Genome Stability

Figure 1B:
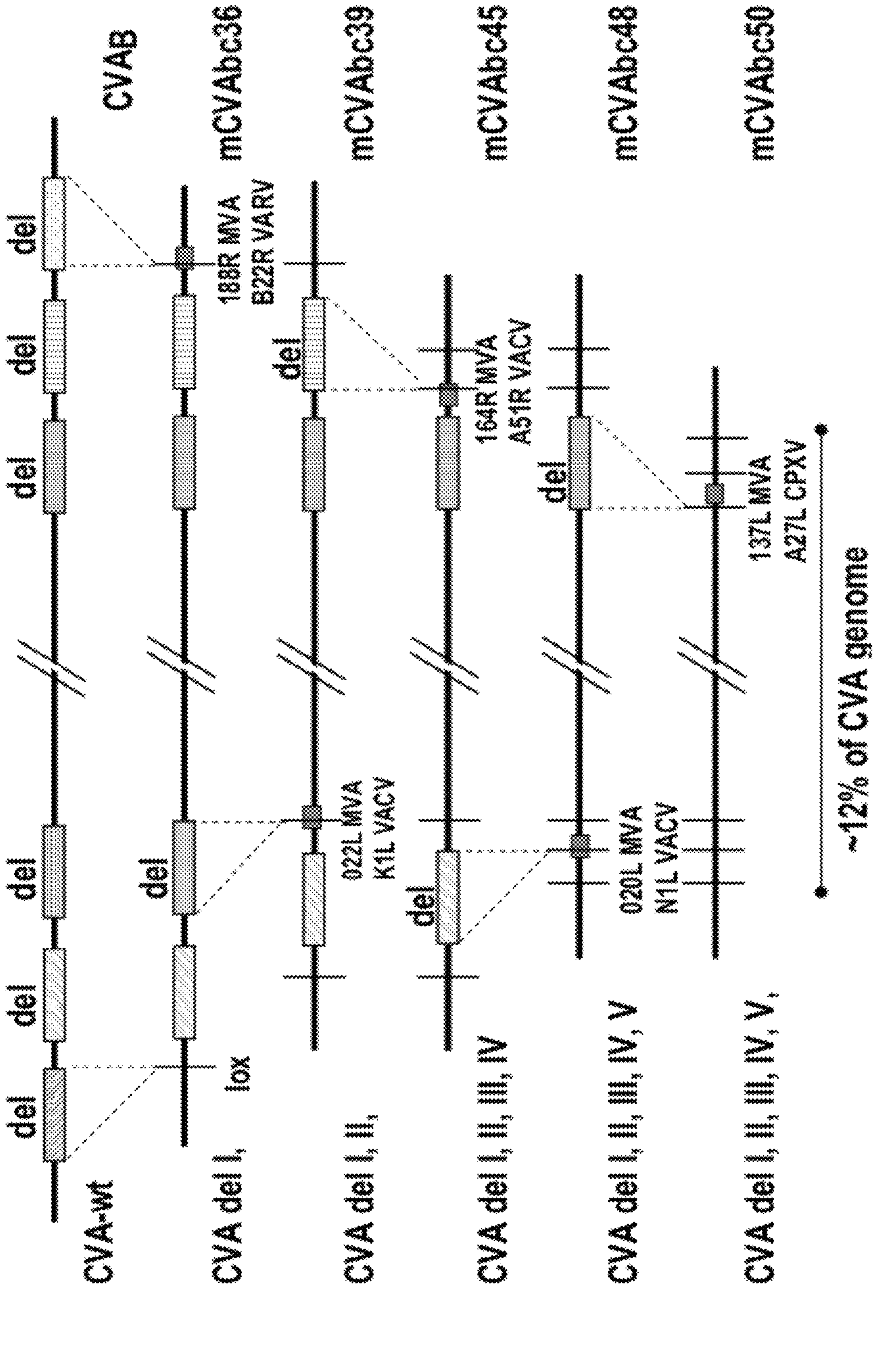

Sequences corresponding to all six major MVA deletions (del I-VI as defined hereinabove) were sequentially removed from $CVA_B$ by BAC mutagenesis to shed light on the genetic basis of the specific MVA phenotype. To exactly mimic the MVA sequence at the deletion sites, we introduced the corresponding truncated or fused MVA ORFs at the newly created deletion sites in CVA. Since in the terminal regions of CVA, most of the ORFs represent fragmented and truncated, presumably non-functional ORFs, the net result of introducing del Ito VI was a mutant $CVA_B$ lacking only 12 full-length genes (Table 1). BAC clones with correct restriction pattern were chosen for reactivation of infectious viruses. We further noted that some BAC clones with aberrant restriction patterns following mutagenesis had incorporated bacterial insertion sequences derived from the *E. coli* DH10B host (4,15). To exclude BACs modified by such mobile genetic elements of *E. coli*, we routinely screened all BACs for absence of bacterial insertion sequences by PCR before rescue. All five mutated CVA-BACs were rescued by transfection of BAC-DNA into SFV-infected BHK cells and the resulting mutant CVAs were passaged on CEF cells to remove the helper virus. The rescued CVA deletion mutants were named mCVAbc36, -39, -45, -48 and -50 (FIG. 1B). We determined the complete coding sequences from ORF CVA001 to ORF CVA229 of the genomes of reactivated mutants mCVAbc39 and mCVAbc50. Except for the deliberately introduced mutations, no additional changes in the two genomic sequences comprising approx. 179,750 and 167,700 nucleotides, respectively, were observed. This result confirmed the suitability of the BAC system for the introduction of multiple mutations into VACV genomes.

Replication Behaviour and Cytopathic Effect of CVA Deletion Mutants

Figure 3A:
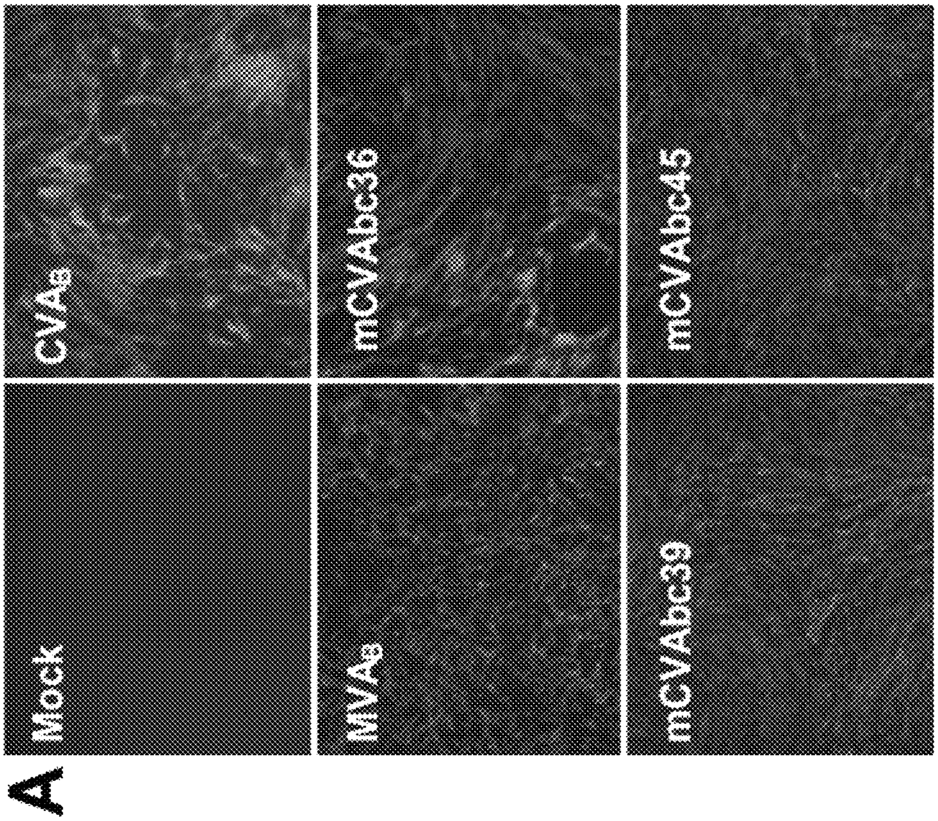

Host range of the various CVA mutants in cell culture was first characterized by visual inspection of spread of the mutants through cell monolayers. For this, primary CEF cells and a panel of 14 permanent cell lines from seven different species were used. Results are shown as a score on an arbitrary scale representing the number of cells showing green fluorescence due to eGFP expression by the mutant viruses. Gross alterations in viral spread were neither observed in primary CEF cells nor in 12 of the 14 cell lines for any of the mutants (Table 2). The only exceptions were noted with the two cell lines RK 13 and SIRC which are of rabbit origin. All mutants containing deletion II (mutants mCVAbc39-50) were unable to spread in these cells. Introduction of deletion II results in functional inactivation of the K1L gene (Table 1). This has been previously shown to strongly impair replication efficiency of the respective vaccinia virus in RK13 cells (24, 33). The cytopathic effect (CPE) in CEFs of all mutants containing more than the two major deletions I and IV was different from $CVA_B$ and was more similar to the CPE caused by $MVA_B$ in these primary cells (FIG. 3A). CEF monolayers infected with mutants mCVAbc39-50 showed a lower degree of cell rounding. Only mCVAbc36 still showed a CPE like wild-type $CVA_B$ (FIG. 3A). In BHK-21 cells which are also permissive for MVA, all CVA deletion mutants showed a wild-type like CPE (data not shown).

TABLE 1

| CVA mutant | | | | | deleted full length gene* | gene function |
|---|---|---|---|---|---|---|
| del I, II, III, IV, V, VI | del I, II, III, IV, V | del I, II, III, IV | del I, II, IV | I, IV | C12L | serine protease inhibitor (serpin) SPI-1 |
| | | | | | M2L | MEK/ERK signalling inhibitor |
| | | | | | K1L | host range protein, NFkB inhibitor |
| | | | | | A52R | TLR/IL-1 R signalling inhibitor |
| | | | | | A53R | soluble TNF receptor (CrmC) |
| | | | | | C5L | 24.5k kelch-like protein |
| | | | | | C4L | 28.8k hypothetical protein |
| | | | | | C3L | complement control protein |
| | | | | | C2L | kelch-like protein, modulator of inflammation |
| | | | | | C1L | 26.4k hypothetical protein |
| | | | | | N1L | inhibitor of apoptosis and TNF-R/TLR signalling |
| | | | | | A26L | p4c protein, directs virus particles into A-type inclusion bodies |

TABLE 2

| | | | | Virus spread[a] | | | | | | |
|---|---|---|---|---|---|---|---|---|---|---|
| Cell line | Species | Organ | Morphology | $MVA_B$ | $CVA_B$ | mCVAbc36 | mCVAbc39 | mCVAbc45 | mCVAbc48 | mCVAbc50 |
| CEF | Chicken | Embryo | Fibroblast | +++ | +++ | +++ | +++ | +++ | +++ | +++ |
| BHK-21 | Syrian hamster | Kidney | Fibroblast | +++ | +++ | +++ | +++ | +++ | +++ | +++ |
| 143B | Human | Bone | Fibroblast | − | +++ | +++ | +++ | +++ | +++ | +++ |
| 293 | Human | Kidney | Epithelial | − | +++ | +++ | +++ | +++ | +++ | +++ |
| HaCat | Human | Skin | Keratinocyte | − | +++ | +++ | +++ | +++ | +++ | +++ |
| Hela | Human | Cervix | Epithelial | − | +++ | +++ | +++ | +++ | +++ | +++ |
| MRC-5 | Human | Lung | Fibroblast | − | +++ | +++ | +++ | +++ | +++ | +++ |
| BS-C-1 | African green monkey | Kidney | Epithelial | + | +++ | +++ | +++ | +++ | +++ | +++ |
| CV-1 | African green monkey | Kidney | Fibroblast | + | +++ | +++ | +++ | +++ | +++ | +++ |
| Vero | African green monkey | Kidney | Fibroblast | ++ | +++ | +++ | +++ | +++ | +++ | +++ |

TABLE 2-continued

| | | | | Virus spread[a] | | | | | | |
|---|---|---|---|---|---|---|---|---|---|---|
| Cell line | Species | Organ | Morphology | $MVA_B$ | $CVA_B$ | mCVAbc36 | mCVAbc39 | mCVAbc45 | mCVAbc48 | mCVAbc50 |
| Balb/ 3T12-3 | Mouse | Embryo | Fibroblast | − | +++ | +++ | +++ | +++ | +++ | +++ |
| MDCK | Dog | Kidney | Epithelial | − | + | + | + | + | + | + |
| RK-13 | Rabbit | Kidney | Epithelial | − | +++ | +++ | − | − | − | − |
| SIRC | Rabbit | Cornea | Fibroblast | − | ++ | ++ | − | − | − | − |
| IEC-6 | Rat | Small intestine | Epithelial | +(+) | +++ | +++ | +++ | +++ | +++ | +++ |

Figure 3B:
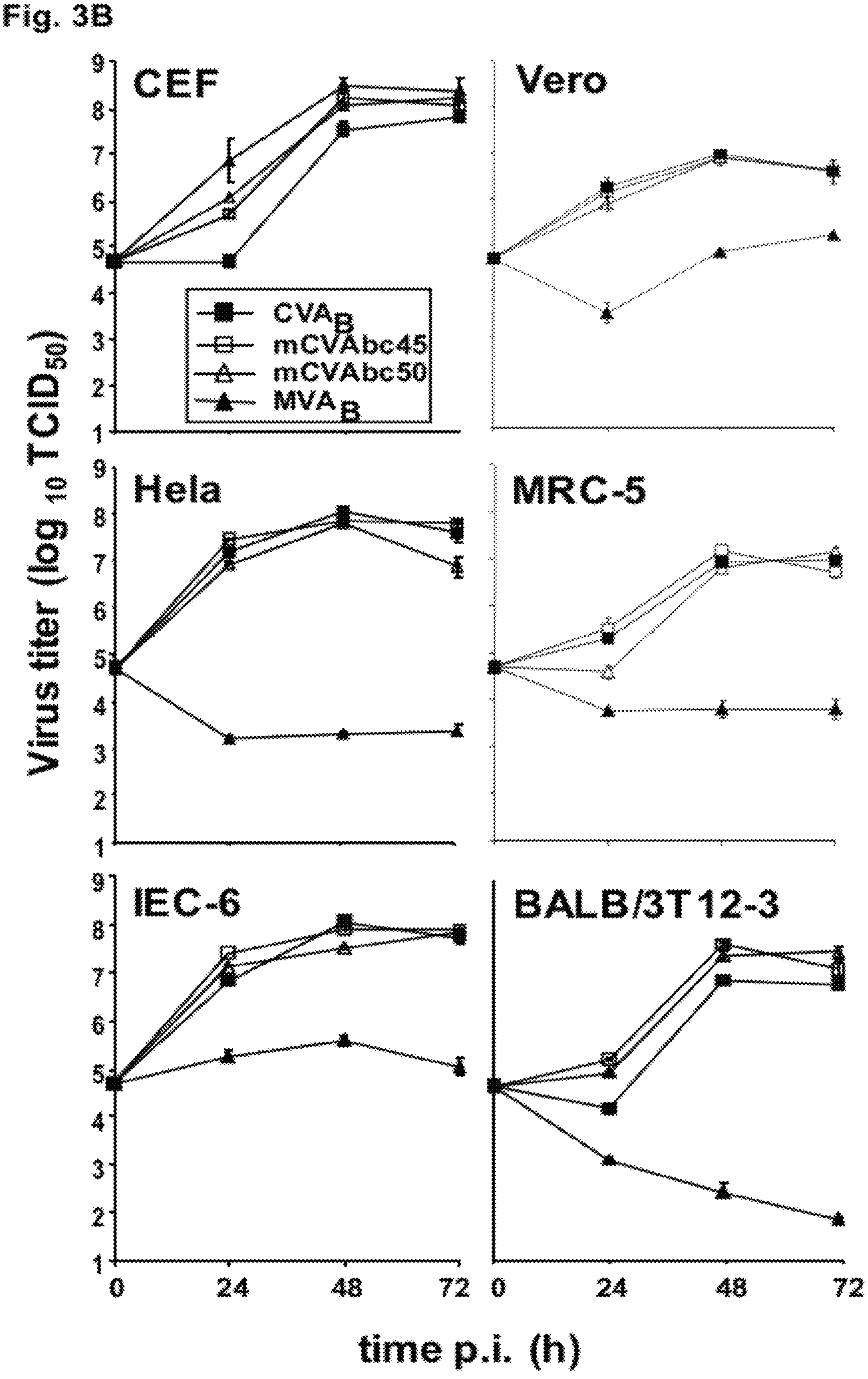

Replication characteristics of the CVA mutants containing MVA-like deletions were examined in further detail in selected cell lines by multi-cycle replication analysis. Replication kinetics of all mutant viruses in primary CEF cells as well as in the human cell lines HeLa and MRC-5 and in the murine cell line BALB/3T12-3 were essentially unaltered compared to $CVA_B$ (FIG. 3B) and thus confirmed our previous conclusions based on visual inspection of viral spread (see Table 2). For reasons of clarity, only data of mutants mCVAbc45 and mCVAbc50 are shown in FIG. 3B. Despite the MVA-like CPE of mutants mCVAbc39-50 in CEF cells, these mutants did not reach the replication efficiency of MVA (FIG. 3B). In contrast, $MVA_B$ showed no replication human cell lines (FIG. 3B) as expected from previous analysis (31). In Vero cells, which are semi-permissive for MVA (20), all CVA mutants showed a very similar replication behaviour with no apparent alteration in replication capacity compared to $CVA_B$ (FIG. 3B).

In rat IEC-6 cells MVA-BN® as well as $MVA_B$ formed small foci of infected cells and thus appeared to be able to replicate and spread to a limited extent in this cell line similar to Vero cells (data not shown and FIG. 3B). Thus, IEC-6 cells are semi-permissive for MVA by the categories defined in a previous report (7). However, in contrast to previous observations (23), IEC-6 cells were clearly not fully permissive for $MVA_B$. All CVA mutants replicated with a similar efficiency as $CVA_B$ in this rat cell line (FIG. 3B).

Taken together, combined introduction of all six major MVA deletions into CVA and deletion of 31 ORFs did not grossly alter the replication capacity of the resulting mutant virus in mammalian cell lines of various species including human, mouse, monkey, hamster, dog, and rat with the sole exception of rabbit cells due to inactivation of the K1L gene.

Virulence of CVA Mutants Containing MVA-Like Deletions in Balb/c Mice

To determine the virulence of CVA mutants containing up to six MVA-like large deletions, BALB/c mice were infected intranasally with a sublethal dose of $3\times10^5$ $TCID_{50}$ per mouse of the different mutants as well as with $CVA_B$ and $MVA_B$. At this inoculation dose, mice infected with $CVA_B$ showed a maximum weight loss of approximately 15-20% and clinical disease peaked at day 6 p.i. (FIG. 4A, C). Weight loss and clinical disease induced by mutants CVAbc36-45 was even more pronounced than after infection with $CVA_B$ indicating a slightly enhanced virulence of these mutants compared to the parental $CVA_B$ (FIG. 4A, C). Of note, these CVA mutants were still less pathogenic than the mouse-adapted VACV strain Western Reserve which was uniformly lethal at a dose of $3\times10^5$ $TCID_{50}$ in BALB/c mice (data not shown). In contrast, mice infected with mutants mCVAbc48 and mCVAbc50 showed reduced weight loss (FIG. 4B) and disease symptoms (FIG. 4D) compared to $CVA_B$.

To compare the pathogenicity of the CVA mutants after infection with a lethal dose of virus, BALB/c mice were intranasally infected with $5\times10^7$ $TCID_{50}$ per mouse of the respective virus mutants. Infection with $CVA_B$ or any of the CVA mutants caused severe weight loss in all mice, whereas $MVA_B$ was completely apathogenic (FIG. 4E, F). All mice infected with $CVA_B$ and mutant mCVAbc36 died (FIG. 4G). In contrast, all mice infected with mCVAbc48 and more than 80% of mice infected with mCVAbc50 survived (FIG. 4H and data not shown). Only one animal infected with mCVAbc50 succumbed to the infection in one out of two independent experiments. Although most mice infected with mCVAbc48 and bc50 survived, they showed significant weight loss which was only slightly reduced compared to animals infected with $CVA_B$ (FIG. 4F). Unexpectedly, most mice infected with high doses of mutant mCVAbc39 also survived the infection (FIG. 4E, G). The reason for the different virulence phenotype of mCVAbc39 at low and high challenge doses is presently unclear. A challenge dose of $1\times10^7$ $TCID_{50}$ had similar effects compared to a dose of $5\times10^7$ $TCID_{50}$ (data not shown). Hence, CVA mutants containing deletions I-V and I-VI were moderately attenuated and the effect was independent of the inoculation dose used. In contrast, the mutants containing up to four deletions were either not attenuated, or they were even slightly more pathogenic than the wild-type CVA at a low inoculation dose. Mutant mCVAbc39 showed an unexpected phenotype in that it was slightly attenuated at higher inoculation doses but showed enhanced virulence at a low inoculation dose (FIG. 4). Clearly, unlike $MVA_B$, even mCVAbc50 still showed considerable virulence in BALB/c mice (FIG. 4). Thus, deletion or truncation of 12 full-length genes and a total of 31 ORFs contained in the six major MVA deletions (Table 1) only moderately decreased the virulence of CVA in the BALB/c mouse intranasal challenge model.

The finding of a discontinuous pattern of attenuation was supported by the analysis of viral titers in lungs of mice at six days after inoculation with a dose of $3\times10^5$ $TCID_{50}$ when severity of disease usually peaked. Titers were slightly but non-significantly higher after infection with mutants CVAbc36 and mCVAbc39 compared to $CVA_B$ ($p=0.06$ by Student's t test)(FIG. 4I) reflecting their enhanced virulence. In contrast, titers were decreased by more than 90% at day six after infection with mCVAbc48 and mCVAbc50 compared to $CVA_B$ (FIG. 4I, $p<0.001$) corroborating the phenotypic finding of reduced virulence of these mutants.

Determinants of mCVAbc48 Attenuation

Figure 5C:
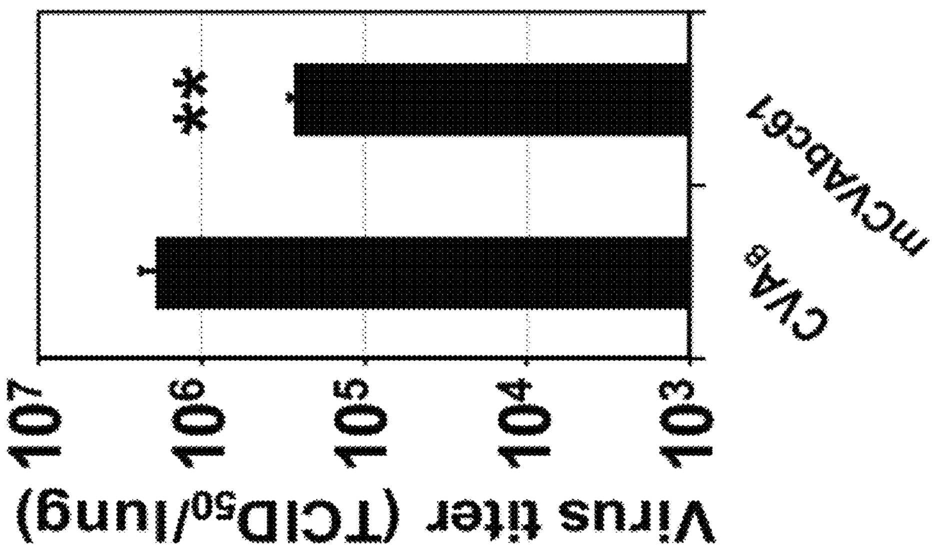

Attenuation of mCVAbc48 and mCVAbc50 at low as well as high inoculation doses indicated that introduction of deletion V was mainly responsible for the observed overall attenuation of these mutants (see Table 1). Deletion V encompasses ORFs C5L-C1L and leads to a frameshift in the N1L ORF causing an altered amino acid sequence of the C-terminal 23 residues of N1 and shortening of the N1 ORF by 4 amino acids. To determine whether deletion V is sufficient to reproduce the attenuated phenotype of mCVAbc48, we separately deleted the sequence corresponding to del V from wild-type $CVA_B$. The resulting mutant mCVAbc61 had CVA-like replication characteristics in HeLa, CEF and BALB/3T12-3 cells and did not show the altered CPE phenotype observed with mutants mCVAbc39 to mCVAbc50 (data not shown). The latter result supported the conclusion that mainly the presence of deletion II was responsible for the altered CPE. Upon intranasal infection with $3\times10^5$ $TCID_{50}$ of virus, mCVAbc61 showed an attenuated phenotype which was even slightly more distinct than the attenuation observed with mutant mCVAbc48 (FIG. 5A, B). Viral titers in lungs of mCVAbc61 infected mice were significantly reduced compared to wild-type $CVA_B$ (FIG. 5C). Thus, deletion V contributed most to the attenuated phenotype of mCVAbc48.

Although attenuation of CVA mutants with deletions of up to 31 ORFs was moderate at most, thorough analysis of the mutant's virulence revealed some interesting aspects elucidating the genetic basis of poxvirus pathogenicity. Two patterns of attenuation emerged depending on the inoculation dose. At a low inoculation dose, virulence increased with deletion of sequences corresponding to del I and IV (mCVAbc36) and then gradually decreased (FIG. 6). Only mutants from which sequences corresponding to del I-V and I-VI had been deleted were less virulent than wild-type CVA. At high inoculation doses virulence was again most clearly decreased when sequences corresponding to five or all six deletions were removed. An exception was mutant mCVAbc39 which was similarly attenuated like mCVAbc48 (FIG. 6). Thus, the net effect of cumulative deletions is not simply the sum of small loss-of-fitness effects generated by sequential introduction of the six deletions. Instead, deletion of sequences corresponding to del I and IV was disease-enhancing at least at a low inoculation dose. Deletion of the next sequences compensated the disease-enhancing effects of deletions I and IV, but only after a sequence corresponding to del V was a detectable attenuation achieved compared to the original $CVA_B$ (FIG. 6). The disease-enhancing effect might be caused by a loss of immunomodulators dampening the immune response and might thus represent an immunopathology due to stronger local or systemic immune responses. Moreover, virulence patterns were dose-dependent. Mutant mCVAbc39 showed a slight attenuation at high inoculation doses which was not detectable at low doses (FIG. 6). Thus, when high inoculation doses were used, a non-linear pattern of attenuation emerged upon accumulation of gene deletions.

REFERENCE LIST

1. Altenburger, J. U.S. Pat. No. 5,185,146. 1993. Ref Type: Patent
2. Altenburger, W., C. P. Suter, and J. Altenburger. 1989. Partial deletion of the human host range gene in the attenuated vaccinia virus MVA. Arch. Virol. 105:15-27.
3. Antoine, G., F. Scheiflinger, F. Dorner, and F. G. Falkner. 1998. The complete genomic sequence of the modified vaccinia Ankara strain: comparison with other orthopoxviruses. Virology 244:365-396.
4. Astua-Monge, G., A. Lyznik, V. Jones, S. A. Mackenzie, and C. E. Vallejos. 2002. Evidence for a prokaryotic insertion-sequence contamination in eukaryotic sequences registered in different databases. Theor. Appl. Genet. 104:48-53.
5. Blanchard, T. J., A. Alcami, P. Andrea, and G. L. Smith. 1998. Modified vaccinia virus Ankara undergoes limited replication in human cells and lacks several immunomodulatory proteins: implications for use as a human vaccine. J. Gen. Virol. 79:1159-1167.
6. Boukamp, P., R. T. Petrussevska, D. Breitkreutz, J. Hornung, A. Markham, and N. E. Fusenig. 1988. Normal keratinization in a spontaneously immortalized aneuploid human keratinocyte cell line. J. Cell Biol. 106:761-771.
7. Carroll, M. W. and B. Moss. 1997. Host range and cytopathogenicity of the highly attenuated MVA strain of vaccinia virus: propagation and generation of recombinant viruses in a nonhuman mammalian cell line. Virology 238: 198-211.
8. Chakrabarty, K., W. Wu, J. L. Booth, E. S. Duggan, N. N. Nagle, K. M. Coggeshall, and J. P. Metcalf. 2007. Human lung innate immune response to *Bacillus anthracis* spore infection. Infect. Immun. 75:3729-3738.
9. Chaplin, P., Howley, P., and Meisinger, C. U.S. Pat. No. 6,913,752 B2. 2005. Ref Type: Patent
10. Datsenko, K. A. and B. L. Wanner. 2000. One-step inactivation of chromosomal genes in *Escherichia coli* K-12 using PCR products. Proc. Natl. Acad. Sci. U.S. A 97:6640-6645.
11. Domi, A. and B. Moss. 2002. Cloning the vaccinia virus genome as a bacterial artificial chromosome in *Escherichia coli* and recovery of infectious virus in mammalian cells. Proc. Natl. Acad. Sci. U.S. A 99:12415-12420.
12. Drexler, I., K. Heller, B. Wahren, V. Erfle, and G. Sutter. 1998. Highly attenuated modified vaccinia virus Ankara replicates in baby hamster kidney cells, a potential host for virus propagation, but not in various human transformed and primary cells. J. Gen. Virol. 79:347-352.
13. Falkner, F. G. and B. Moss. 1990. Transient dominant selection of recombinant vaccinia viruses. J. Virol. 64:3108-3111.
14. Kaerber, G. 1931. Beitrag zur kollektiven Behandlung pharmakologischer Reihenversuche. Arch Exp Pathol Pharmakol. 162:480-483.
15. Kovarik, A., M. A. Matzke, A. J. Matzke, and B. Koulakova. 2001. Transposition of IS10 from the host *Escherichia coli* genome to a plasmid may lead to cloning artefacts. Mol. Genet. Genomics 266:216-222.
16. Mayr, A., V. Hochstein-Mintzel, and H. Stickl. 1975. Abstammung, Eigenschaften und Verwendung des attenuierten Vaccinia-Stammes MVA. Infection 3:6-14.
17. Mayr, A. and E. Munz. 1964. [Changes in the vaccinia virus through continuing passages in chick embryo fibroblast cultures]. Zentralbl. Bakteriol. Orig. 195:24-35.
18. Mayr, A., H. Stickl, H. K. Muller, K. Danner, and H. Singer. 1978. [The smallpox vaccination strain MVA: marker, genetic structure, experience gained with the parenteral vaccination and behavior in organisms with a debilitated defence mechanism (author's transl)]. Zentralbl. Bakteriol. [B] 167:375-390.
19. Meisinger-Henschel, C., M. Schmidt, S. Lukassen, B. Linke, L. Krause, S. Konietzny, A. Goesmann, P. Howley, P. Chaplin, M. Suter, and J. Hausmann. 2007. Genomic sequence of chorioallantois vaccinia virus Ankara, the ancestor of modified vaccinia virus Ankara. J. Gen. Virol. 88:3249-3259.
20. Meyer, H., G. Sutter, and A. Mayr. 1991. Mapping of deletions in the genome of the highly attenuated vaccinia virus MVA and their influence on virulence. J. Gen. Virol. 72:1031-1038.
21. Moss, B., M. W. Carroll, L. S. Wyatt, J. R. Bennink, V. M. Hirsch, S. Goldstein, W. R. Elkins, T. R. Fuerst, J. D. Lifson, M. Piatak, N. P. Restifo, W. Overwijk, R. Chamberlain, S. A. Rosenberg, and G. Sutter. 1996. Host range restricted, non-replicating vaccinia virus vectors as vaccine candidates. Adv. Exp. Med. Biol. 397:7-13.

22. O'Connor, M., M. Peifer, and W. Bender. 1989. Construction of large DNA segments in *Escherichia coli*. Science 244:1307-1312.

23. Okeke, M. I., O. Nilssen, and T. Traavik. 2006. Modified vaccinia virus Ankara multiplies in rat IEC-6 cells and limited production of mature virions occurs in other mammalian cell lines. J. Gen. Virol. 87:21-27.

24. Perkus, M. E., S. J. Goebel, S. W. Davis, G. P. Johnson, K. Limbach, E. K. Norton, and E. Paoletti. 1990. Vaccinia virus host range genes. Virology 179:276-286.

25. Perkus, M. E., S. J. Goebel, S. W. Davis, G. P. Johnson, E. K. Norton, and E. Paoletti. 1991. Deletion of 55 open reading frames from the termini of vaccinia virus. Virology 180:406-410.

26. Reyrat, J. M., V. Pelicic, B. Gicquel, and R. Rappuoli. 1998. Counterselectable markers: untapped tools for bacterial genetics and pathogenesis. Infect. Immun. 66:4011-4017.

27. Spearman, C. 2010. The method of "right and wrong cases" ("constant stimuli") without Gauss's formulae. British Journal of Psychology 2:227-242.

28. Staib, C., I. Drexler, and G. Sutter. 2004. Construction and isolation of recombinant MVA. Methods Mol. Biol. 269: 77-100.

29. Stickl, H., V. Hochstein-Mintzel, and H. C. Huber. 1973. [Primary vaccination against smallpox after preliminary vaccination with the attenuated vaccinia virus strain MVA and the use of a new "vaccination stamp"]. Munch. Med. Wochenschr. 115:1471-1473.

30. Stickl, H., V. Hochstein-Mintzel, A. Mayr, H. C. Huber, H. Schafer, and A. Holzner. 1974. [MVA vaccination against smallpox: clinical tests with an attenuated live vaccinia virus strain (MVA) (author's transl)]. Dtsch. Med. Wochenschr. 99:2386-2392.

31. Suter, M., C. Meisinger-Henschel, M. Tzatzaris, V. Hulsemann, S. Lukassen, N. H. Wulff, J. Hausmann, P. Howley, and P. Chaplin. 2009. Modified vaccinia Ankara strains with identical coding sequences actually represent complex mixtures of viruses that determine the biological properties of each strain. Vaccine 27:7442-7450.

32. Sutter, G. and B. Moss. 1992. Nonreplicating vaccinia vector efficiently expresses recombinant genes. Proc. Natl. Acad. Sci. U.S. A 89:10847-10851.

33. Sutter, G., A. Ramsey-Ewing, R. Rosales, and B. Moss. 1994. Stable expression of the vaccinia virus K1L gene in rabbit cells complements the host range defect of a vaccinia virus mutant. J. Virol. 68:4109-4116.

34. Tartaglia, J., M. E. Perkus, J. Taylor, E. K. Norton, J. C. Audonnet, W. I. Cox, S. W. Davis, H. J. van der, B. Meignier, M. Riviere, B. Languet, and E. Paoletti. 1992. NYVAC: a highly attenuated strain of vaccinia virus. Virology 188:217-232.

35. Wang, S., Y. Zhao, M. Leiby, and J. Zhu. 2009. A new positive/negative selection scheme for precise BAC recombineering. Mol. Biotechnol. 42:110-116.

36. Wyatt, L. S., M. W. Carroll, C. P. Czerny, M. Merchlinsky, J. R. Sisler, and B. Moss. 1998. Marker rescue of the host range restriction defects of modified vaccinia virus Ankara. Virology 251:334-342.

37. Yao, X. D. and D. H. Evans. 2003. High-frequency genetic recombination and reactivation of orthopoxviruses from DNA fragments transfected into leporipoxvirus-infected cells. J. Virol. 77:7281-7290.

38. Zhang, Y., J. P. Muyrers, J. Rientjes, and A. F. Stewart. 2003. Phage annealing proteins promote oligonucleotide-directed mutagenesis in *Escherichia coli* and mouse ES cells. BMC. Mol. Biol. 4:1.

39. Zhu, W., Q. Fang, K. Zhuang, H. Wang, W. Yu, J. Zhou, L. Liu, P. Tien, L. Zhang, and Z. Chen. 2007. The attenuation of vaccinia Tian Tan strain by the removal of the viral M1 L-K2L genes. J. Virol. Methods 144:17-26.

40. Huang X, Lu B, Yu W, Fang Q, Liu L, et al. (2009) A Novel Replication-Competent Vaccinia Vector MVTT Is Superior to MVA for Inducing High Levels of Neutralizing Antibody via Mucosal Vaccination. PLoS ONE 4(1): e4180. doi:10.1371/journal.pone.0004180

The invention claimed is:

1. A method of preparing a chorioallantois vaccinia virus Ankara deletion variant (dCVA), said method comprising:

(a) providing a vector comprising the genome of chorioallantois vaccinia virus Ankara (CVA);

(b) deleting the sequences corresponding to del I, del II, del III, del IV, del V, and del VI of modified vaccinia Ankara virus (MVA); and (c) isolating the dCVA.

2. The method of claim 1, further comprising the step of measuring the amplification ratio of the dCVA in a human cell line.

3. The method of claim 2, wherein the human cell line is selected from the group consisting of MRC-5 (ATCC CCL-171), 293 and 143B.

4. A chorioallantois vaccinia virus Ankara deletion variant (dCVA) obtained by the method of claim 1, wherein the dCVA replicates in a human cell line with an amplification ratio of greater than 5.

5. The dCVA of claim 4, wherein the dCVA replicates in the MRC-5 (ATCC CCL-171), 293 and 143B cell lines with an amplification ratio of greater than 5.

6. A chorioallantois vaccinia virus Ankara deletion variant (dCVA) obtained by the method of claim 2, wherein the dCVA replicates in a human cell line with an amplification ratio of greater than 5.

7. The dCVA of claim 6, wherein the dCVA replicates in the MRC-5 (ATCC CCL-171), 293 and 143B cell lines with an amplification ratio of greater than 5.

8. A vector comprising the genome of the dCVA of claim 4.

9. A vector comprising the genome of the dCVA of claim 6.

10. The vector of claim 8, wherein the vector is a bacterial artificial chromosome (BAC).

11. The vector of claim 9, wherein the vector is a bacterial artificial chromosome (BAC).

12. An isolated cell comprising the genome of the dCVA of claim 4.

13. An isolated cell comprising the genome of the dCVA of claim 6.

14. A method for determining the effect of a mutation on a chorioallantois vaccinia virus Ankara deletion variant (dCVA) comprising:

(a) providing a vector comprising the genome of a dCVA from which the sequences corresponding to del I, del II, del III, del IV, del V, and del VI of modified vaccinia Ankara virus (MVA) are deleted;

(b) introducing at least one mutation into the dCVA genome in order to obtain a mutated CVA deletion variant (mdCVA); and (c) determining whether the mutation affects the replication of said mdCVA.

15. The method of claim 14, further comprising the step of measuring the amplification ratio of the mdCVA in a human cell line.

16. The method of claim 15, further comprising comparing the amplification ratio of the dCVA with the amplification ratio of the mdCVA in order to determine whether the at least one mutation affects the replication of the mdCVA in the human cell line.

17. The method of claim 14, further comprising determining whether the at least one mutation affects the replication of the mdCVA, the pathogenicity of the mdCVA, or the immunogenicity of the mdCVA in an animal.

18. The method of claim 15, wherein the human cell line is selected form the group consisting of MRC-5 (ATCC CCL-171), 293 and 143B.

19. A method of preparing a mutated chorioallantois vaccinia virus Ankara deletion variant (mdCVA) comprising:

(a) providing the dCVA of claim 4;

(b) introducing at least one mutation into the genome of the dCVA to generate the mdCVA; and (c) isolating the mdCVA.

20. The method of claim 19, further comprising the step of measuring the amplification ratio of the mdCVA in a human cell line.

21. The method of claim 20, further comprising comparing the amplification ratio of the dCVA with the amplification ratio of the mdCVA in order to determine whether the at least one mutation affects the replication of the mdCVA in the human cell line.

22. The method of claim 20, wherein the human cell line is selected from the group consisting of MRC-5 (ATCC CCL-171), 293 and 143B.

23. The method of claim 1, wherein the CVA is CVA-PP as deposited under ECACC accession number 10062901.

* * * * *